United States Patent
Silverman et al.

(10) Patent No.: US 9,657,317 B2
(45) Date of Patent: May 23, 2017

(54) HOST CELLS AND METHOD FOR MAKING ACRYLATE AND PRECURSORS THEREOF USING AN ODD-NUMBERED ALKANE FEEDSTOCK

(71) Applicant: Calysta, Inc., Menlo Park, CA (US)

(72) Inventors: Joshua A. Silverman, Redwood City, CA (US); Tom Purcell, Menlo Park, CA (US); Jon Edward Ness, Menlo Park, CA (US); Effendi Leonard, Randolph, MA (US)

(73) Assignee: Calysta, Inc., Menlo Park, CA (US)

( * ) Notice: Subject to any disclaimer, the term of this patent is extended or adjusted under 35 U.S.C. 154(b) by 61 days.

(21) Appl. No.: 14/344,899

(22) PCT Filed: Oct. 17, 2012

(86) PCT No.: PCT/US2012/060671
§ 371 (c)(1),
(2) Date: Mar. 13, 2014

(87) PCT Pub. No.: WO2013/059362
PCT Pub. Date: Apr. 25, 2013

(65) Prior Publication Data
US 2015/0087036 A1     Mar. 26, 2015

Related U.S. Application Data

(60) Provisional application No. 61/549,133, filed on Oct. 19, 2011.

(51) Int. Cl.
*C12P 7/42* (2006.01)
*C12P 19/32* (2006.01)
(Continued)

(52) U.S. Cl.
CPC ............. *C12P 7/42* (2013.01); *C12N 15/52* (2013.01); *C12P 7/40* (2013.01); *C12P 19/32* (2013.01)

(58) Field of Classification Search
CPC .... C12P 7/42; C12P 19/32; C12P 7/40; C12N 15/52
See application file for complete search history.

(56) References Cited

U.S. PATENT DOCUMENTS

2003/0100744 A1   5/2003   Farinas et al.
2008/0293101 A1   11/2008  Peters et al.
(Continued)

OTHER PUBLICATIONS

Beilen et al., Rubredoxins Involved in Alkane Oxidation., Journal of Bacteriology (2002), vol. 184, pp. 1722-1732.*
(Continued)

*Primary Examiner* — Alexander Kim
(74) *Attorney, Agent, or Firm* — Seed IP Law Group LLP

(57) ABSTRACT

Provided herein is an alkane-metabolizing cell that is unable to convert propionyl-CoA into methylmalonyl-CoA or 2-metylcitrate synthase. Depending on which enzymes are present in the cell, the cell can produce acrylate or a precursor for the same (e.g., propionate, 3-hydroxypropionyl-CoA, 3-hydroxypropionate, acrylyl-CoA) that can be readily converted to acrylate enzymatically (e.g., in the cell) or by chemical treatment. In one embodiment, the cell may contain a cytochrome P450 or alkane oxidase enzyme that allows the production of 3-hydroxypropionyl-CoA, which can be readily converted to 3-hydroxypropionate. In order to make such compounds, the cell may be grown in the presence of an odd-numbered chain alkane (e.g., pentane or heptane), although another odd-numbered chain alkane may be used. In another embodiment, the cell may contain acyl-CoA oxidase, enoyl-CoA hydratase, and hydrolase.

28 Claims, 10 Drawing Sheets

(51) Int. Cl.
    *C12P 7/40*    (2006.01)
    *C12N 15/52*   (2006.01)

(56) References Cited

U.S. PATENT DOCUMENTS

2009/0053783 A1   2/2009   Gokarn et al.
2009/0191599 A1   7/2009   Devroe et al.

OTHER PUBLICATIONS

Kelson et al., Chaperonin-mediated assembly of wild-type and mutant subunits of human propionyl-CoA carboxylase expressed in *Escherichia coli.*, Human Molecular Genetics (1996), vol. 5, pp. 331-337.*

Ginkel et al., Oxidation of Gaseous and Volatile Hydrocarbons by Selected Alkene-Utilizing Bacteria., Applied and Environmental Microbiology (1987), vol. 53, pp. 2903-2907.*

P33006 (last viewed on Jun. 24, 2015).*

Donadio et al. (Erythromycin production in Saccharopolyspora erythraea does not require a functional propionyl-CoA carboxylase., Mol Microbiol. (1996), vol. 19(5), pp. 977-984.*

Kegg Chloroalkane degradation Saccharopolyspora erythraea (last viewed on Dec. 3, 2015).*

Horswill et al., Studies of Propionate Toxicity in *Salmonella enterica* Identify 2-Methylcitrate as a Potent Inhibitor of Cell Growth., The Journal of Biological Chemistry (2001), vol. 276, pp. 19094-19101.*

KEGG *Salmonella enterica* (last viewed on Dec. 4, 2015).*

Branden and Tooze, Introduction to Protein Structure (1999), 2nd edition, Garland Science Publisher, pp. 3-12.*

Guo et al., Protein tolerance to random amino acid change, 2004, Proc. Natl. Acad. Sci. USA 101: 9205-9210.*

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Doughty, et al., "Product repression of alkane monooxygenase expression in Pseudomonas butanovora", J Bacteriol., 2006,188(7):2586-92.

* cited by examiner

HOST CELLS AND METHOD FOR MAKING ACRYLATE AND PRECURSORS THEREOF USING AN ODD-NUMBERED ALKANE FEEDSTOCK

CROSS-REFERENCING

This application claims the benefit of U.S. Provisional Application Ser. No. 61/549,133, filed on Oct. 19, 2011, which application is incorporated by reference herein in its entirety.

BACKGROUND 3-hydroxypropionic acid (3-HP) is a platform chemical that can be readily converted into a variety of valuable products, such as poly(hydroxypropionate), 1,3-propanediol, EEP, acrylamide, malonic acid and acrylic acid.

For example, 3-HP can be dehydrated to produce acrylic acid, which can be polymerized (e.g., with itself or with other monomers such as acrylamide, acrylonitrile, vinyl, styrene, or butadiene) to produce a variety of homopolymers and copolymers that are used in the manufacture of various plastics, coatings, adhesives, elastomers, latex applications, emulsions, leather finishings, and paper coating, as well as floor polishes, and paints. Acrylic acid can also be used as a chemical intermediate for the production of acrylic esters such as ethyl acrylate, butyl acrylate, methyl acrylate, and 2-ethyl hexyl acrylate and superabsorbent polymers (glacial acrylic acid).

SUMMARY

Provided herein is an alkane-metabolizing cell that is unable to convert propionyl-CoA into methylmalonyl-CoA or 2-methylcitrate. Depending on which enzymes are present in the cell, the cell can produce acrylate or a precursor for the same (e.g., propionate, 3-hydroxypropionyl-CoA, 3-hydroxypropionate, acrylyl-CoA) that can be readily converted to acrylate enzymatically (e.g., in the cell or by treating a cell lysate) or by chemical treatment. In one embodiment, the cell may contain a cytochrome P450 or alkane oxidase enzyme that allows the cell to produce 3-hydroxypropionyl-CoA, which can be readily converted to 3-hydroxypropionate. In culture, the cell may be grown in the presence of an odd-numbered chain alkane (e.g., pentane or heptane), although another odd-numbered chain alkane may be used. In another embodiment, the cell may contain acyl-CoA oxidase, enoyl-CoA hydratase, and hydrolase.

DEFINITIONS

Figure 1:
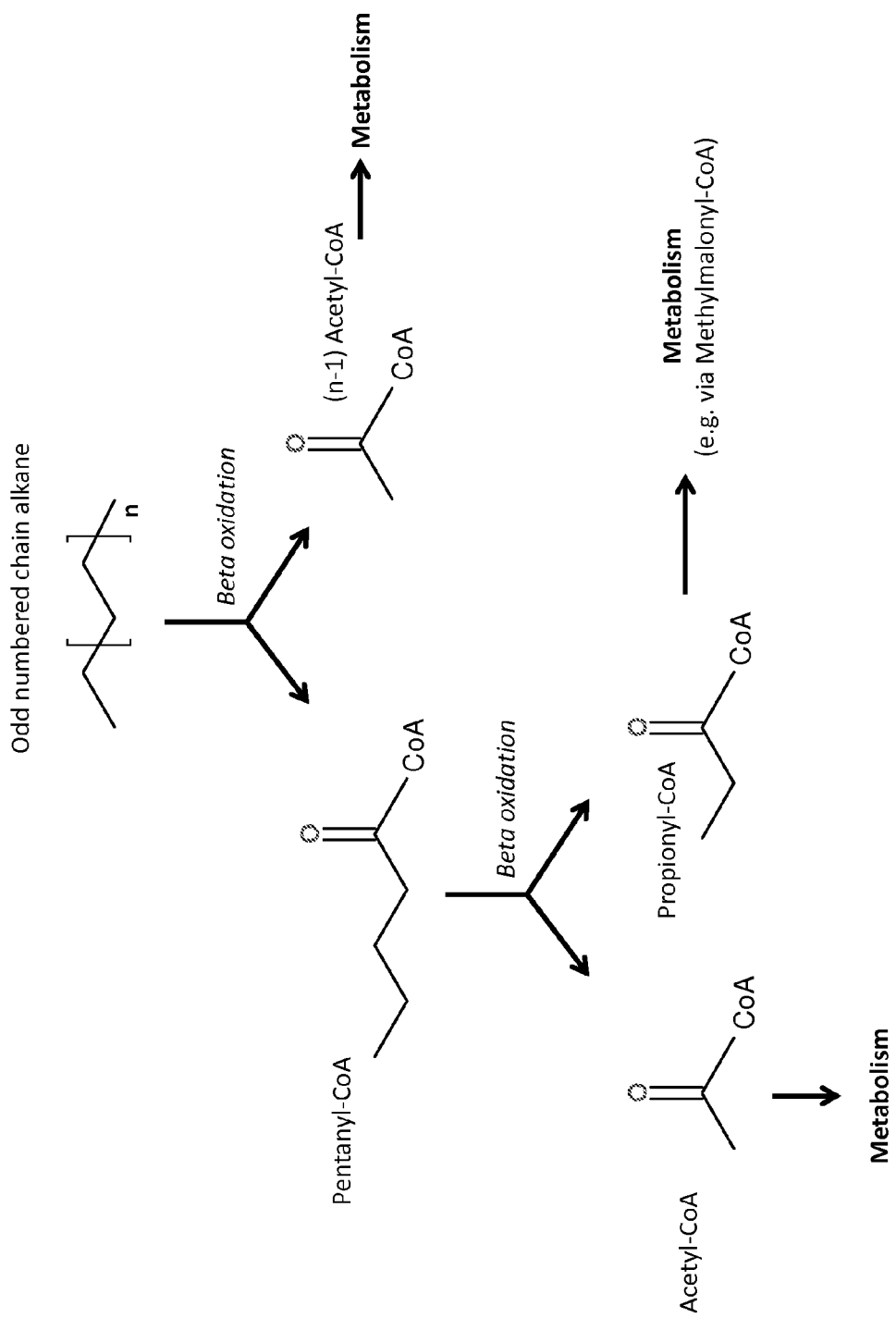
FIG. 1 shows the biochemical pathway for how odd-numbered chain alkanes are metabolized by β-oxidation to produce acetyl-CoA in wild type cells. Acetyl CoA enters the citric acid cycle. Propionyl-CoA, which is produced as a bi-product of the pathway, is converted into methylmalonyl-CoA or 2-methylcitrate and metabolized in the cell.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "contacting" means to bring or put together. As such, a first item is contacted with a second item when the two items are brought or put together, e.g., by touching them to each other or combining them in the same solution.

The terms "protein" and "polypeptide" are used interchangeably herein.

The term "nucleic acid" encompasses DNA, RNA, single stranded or double stranded and chemical modifications thereof. The terms "nucleic acid" and "polynucleotide" are used interchangeably herein.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

The term "construct" refers to any polynucleotide that contains a recombinant nucleic acid. A construct may be present in a vector (e.g., a viral vector) or may be integrated in a genome, for example.

The term "selective marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or 'transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, "expression vector" refers to a DNA construct containing a DNA sequence that is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid," "expression plasmid," and "vector" are often used interchangeably as the plasmid is the most commonly used form of vector at present. However, the invention is intended to include such other forms of expression vectors that serve equivalent functions and which are, or become, known in the art.

As used herein, "corresponding to," refers to a residue at the enumerated position in a protein or peptide, or a residue that is equivalent in position to the enumerated residue in a different protein or peptide. Identifying corresponding amino acids may be done by aligning the sequences and identifying residues that like across from one another in the resultant alignment. In other words, the residue number or residue position of a given polymer is designated with respect to the reference sequence rather than by the actual numerical position of that residue within the given amino acid or polynucleotide sequence.

As used herein, "wild-type", "native" and "naturally-occurring" refers to proteins are those found in nature. The term "wild-type sequence," is used herein to refer to a sequence that is native or naturally occurring in a host cell. The term "non-naturally occurring" refers to proteins that are not found in nature. A "native" protein or nucleic acid is a wild-type sequence that exists in the non-recombinant version of the cell in which it currently resides.

As used herein, the term "isolated" refers to a substance that has been removed from the source in which it naturally occurs. A substance need not be purified in order to be isolated. For example, a protein produced in a host cell is considered isolated when it is removed or released from the cell. A protein contained within a crude cell lysate fraction is considered "isolated" for purposes of the present disclosure.

As used herein, the term "purified" refers to a substance that has been rendered at least partially free of contaminants and other materials that typically accompany it. Substances can be purified to varying degrees. A substance is "substantially pure" when a preparation or composition of the substance contains less than about 1% contaminants. A substance is "essentially pure" when a preparation or composition of the substance contains less than about 5% contaminants. A substance is "pure" when a preparation or composition of the substance contains less than about 2% contaminants. For substances that are "purified to homogeneity," contaminants cannot be detected with conventional analytical methods. The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

The term "heterologous" refers to elements that are not normally associated with each other. For example, if a host cell produces a heterologous protein, that protein that is not normally produced in that host cell. Likewise, a promoter that is operably linked to a heterologous coding sequence is a promoter that is operably linked to a coding sequence that it is not usually operably linked to in a wild-type host cell. The term "homologous", with reference to a polynucleotide or protein, refers to a polynucleotide or protein that occurs naturally in a host cell.

As used herein, the terms "percent sequence identity," "percent identity," and/or "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence in order to effect optimal alignment. The percentage identity is calculated by dividing the number of matched portions in the comparison window by the total number of positions in the comparison window, and multiplying by 100. The number of matched positions in the comparison window is the sum of the number of positions of the comparison polynucleotide or polypeptide in the window that are identical in sequence to the reference polynucleotide or polypeptide and the number of positions of the reference polynucleotide or polypeptide in the comparison window that align with a gap in the comparison polynucleotide or polypeptide. Determination of optimal alignment and percent sequence identity is performed using the BLAST and BLAST 2.0 algorithms (see, e.g., Altschul et al., 1990, J. Mol. Biol. 215:403-410 and Altschul et al., 1997, Nucleic Acids Res. 25(17):3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, 1990, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989, Proc. Nat'l Acad. Sci. USA 89:10915). Numerous other algorithms are available that function similarly to BLAST in providing percentage identity between sequences.

Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., 1995 Supplement).

As used herein, the term "reference sequence" refers to a specified sequence to which another sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered, variant and/or altered sequences.

As used herein, the term "comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, the term "amino acid substitution" refers to the replacement of a first amino acid with any other amino acid.

As used herein, the term "conservative amino acid substitution" refers to the replacement of a first amino acid with a second amino acid having the same properties as the first amino acid. Such groups are defined as follows: group 1: gly, ala; group 2: val, ile, leu; group 3: asp, glu; group 4: asn, gln; group 5: ser, thr; group 6: lys, arg; and group 7: phe, tyr.

As used herein, the term "alkane-metabolizing cell" refers to a cell that can metabolize an exogenously-supplied alkane via β-oxidation (i.e., oxidation at the β-carbon atom) to produce acetyl-CoA. Such cells may be bacterial or fungal, although other cells may be employed. How alkanes are metabolized by bacteria is described in Wentzel et al (App. Microbiol. Biotechnol. 2007 76: 1209-1221). An alkane-metabolizing cell may be able to metabolize: a) both long chain alkanes (which have at least 10 carbons) and short-chain alkanes (which have less than 10 carbons), b) only long chain alkanes, or c) only short-chain alkanes.

As used herein, the term "odd-numbered chain alkane" refers to an alkane with an odd number (e.g., 3, 5, 7, 9, 11, 13, 15, 17, 19, 21, etc.) of carbon atoms. The omega carbon of such an alkane is the carbon atom that is at the end that is not oxidized by β-oxidation. In other words, the omega carbon of an alkane is at opposite end to the end that is β-oxidized.

As used herein, the term "enzyme that can hydroxylate the omega carbon of an alkane or a β-oxidation product of the same" and grammatical equivalents thereof refers to a hydroxylase that can hydroxylate the omega carbon of an alkane, as well as products made by β-oxidation of such an alkane to produce, e.g., hydroxyalkane, hydroxyalkanoic acid, hydroxyalkanyl-CoA, etc. Metabolism of an odd-numbered chain alkane by β-oxidation produces propionyl-CoA. As such, this definition also includes enzymes that hydroxylate the omega carbon of propionyl-CoA. As will be discussed in greater detail below, such an enzyme may be able to use: a) an alkane itself and all β-oxidation products of the same as a substrate, or b) some but not all of those molecules as a substrate.

As used herein, the term "pentane metabolizing cell" refers to a cell that is able to metabolize exogenously-supplied pentane via β-oxidation to produce acetyl-CoA and propionyl-CoA.

As used herein, the term "unable to convert propionyl-CoA into methylmalonyl-CoA or 2-methylcitrate" refers to a cell that is blocked in its ability to produce methylmalonyl-CoA from propionyl-CoA. Such a blocking may be done by inactivating one or more propionyl-CoA carboxylase or 2-methylcitrate synthase genes in the cell, although other methods may be available.

An "inactivated gene" is a locus of a genome that, prior to its inactivation, was capable of producing a protein, i.e., capable of being transcribed into an RNA that can be translated to produce a full length polypeptide. A gene is inactivated when it not transcribed and translated into full length catalytically active protein. A gene may be inactivated by altering a sequence required for its transcription, by altering a sequence required for RNA processing, e.g., poly-A tail addition, by altering a sequence required for translation, for example. A deleted gene, a gene containing a deleted region, a gene containing a rearranged region, a gene having an inactivating point mutation or frameshift and a gene containing an insertion are types of inactivated gene. A gene may also be inactivated using antisense or any other method that abolishes expression of that gene.

Other definitions of terms may appear throughout the specification.

DESCRIPTION OF EXEMPLARY EMBODIMENTS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

Host Cells

A parental version of the subject host cell (i.e., cells that are not modified in the way described below) is able to metabolize exogenously-supplied odd-numbered chain alkanes via β-oxidation to produce acetyl-CoA and propionyl-CoA according to the pathway illustrated in FIG. 1. In these cells, in most cases, acetyl-CoA enters the citric acid and/or glyoxylic acid cycles and is metabolized. Likewise, in many cases, propionyl-CoA is converted to methylmalonyl-CoA which may be converted to succinyl-CoA, an intermediate in the tricarboxylic acid cycle. Propionyl-CoA may also be converted into 2-methylcitrate. In particular cases, a parental version of the subject host cell may be able to metabolize exogenously-supplied pentane to acetyl-CoA and propionyl-CoA via the pathway shown in the top part of FIG. 3. A host cell that is supplied with a long odd numbered chain alkane (which has at least 11 carbons) or a short odd numbered chain alkane such as pentane should produce both pentanoyl-CoA and propionyl-CoA because those intermediates are both produced regardless of the length of alkane supplied.

Figure 3:
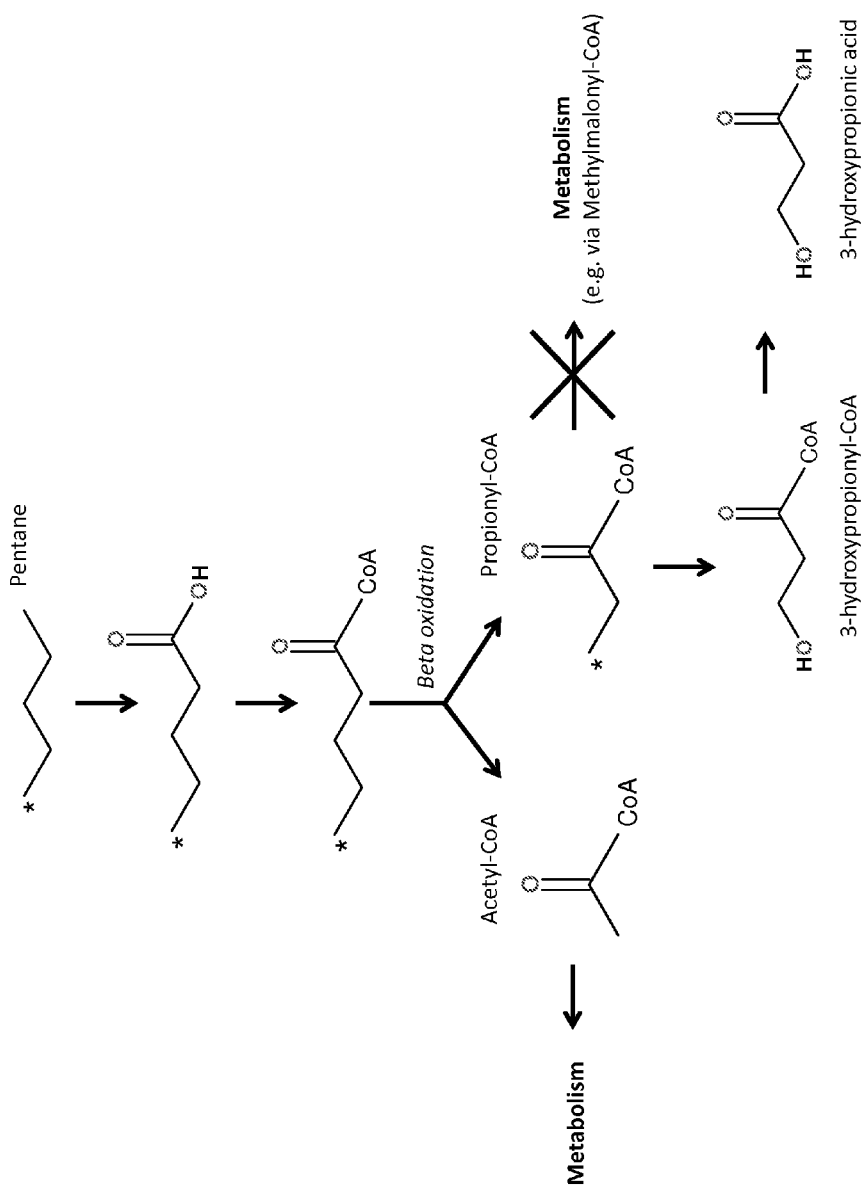
FIG. 3 shows a biochemical pathway describing how 3-hydroxypropionate can be made in a subject cell. This exemplary pathway uses pentane as a feedstock, although other odd-numbered chain alkanes may be used. The asterisk indicates the omega carbon atom.

In particular cases, a parental version of a subject host cell may be a pentane metabolizing cell in that it can metabolize pentane to produce acetyl-CoA and propionyl-CoA via the pathway shown in the top part of FIG. 3. As shown in FIG. 3, pentane-metabolizing cells convert pentane to pentanoic acid, and then convert pentanoic acid to pentanoyl-CoA. The pentanoyl-CoA is then converted to acetyl-CoA and propionyl-CoA via β-oxidation. A pentane metabolizing cell may or may not be able to metabolize long chain alkanes in addition to pentane. Alternatively, a pentane metabolizing cell may or may not be able to metabolize shorter alkanes such as propane.

Cells that can metabolize exogenously-supplied odd-numbered chain alkanes via β-oxidation are widely distributed throughout the microbial kingdom and include bacteria *Pseudomonas* (e.g., *P. aeruginosa* and *P. oleovorans*), *Corynebacterium, Mycobacterium, Nocardia* and *Rhodococcus*, and yeast of the genus *Candida, Pichia, Yarrowia* and *Torulopsis*, most of which are genetically manipulatable by known methods. *Candida tropicalis, Yarrowia lipolytica*, and *Rhodococcus opacus* are examples of host cells that can be employed herein, although a multitude of others are available.

As noted above, the subject cell is unable to convert propionyl-CoA into methylmalonyl-CoA or 2-methylcitrate; and therefore accumulates propionyl-CoA. Such a cell may be made by abolishing the expression of the enzyme that converts propionyl-CoA to methylmalonyl-CoA or 2-methylcitrate in the cell. This enzyme, propionyl-CoA carboxylase or 2-methylcitrate synthase, may be abolished in a host cell using a number of methods, including methods that employ antisense molecules, or ribozymes, for example. In certain embodiments, expression of propionyl-CoA carboxylase or 2-methylcitrate synthase may be abolished by inactivating all copies of the corresponding genes in the cell. The DNA sequences of several hundred propionyl-CoA carboxylase genes and the proteins encoded by those genes have been determined and deposited into NCBI's Genbank database. The enzyme activities are referred to as either propionyl-CoA carboxylase (EC 6.4.1.3) or methylmalonyl-coA decarboxylase (EC 4.1.1.41) or 2-methylcitrate synthase (EC 2.3.3.5). Exemplary propionyl-CoA carboxylase that can be inactivated include those defined by Genbank Accession Nos. XP_503870.1 and/or XP_502210.1 (*Yarrowia lipolytica*), and YP_002780756.1 (pccB) (*Rhodococcus opacus*). Exemplary of 2-methylcitrate synthase that can be inactivated include those defined by Genbank Accession No. XP_503380.1 (*Yarrowia lipolytica*). Orthologs of these genes are readily identifiable using bioinformatics or routine molecular techniques.

When fed with an odd-numbered chain alkane, a host cell that is unable to convert propionyl-CoA into methylmalonyl-CoA may contain less than 1% of the methylmalonyl-CoA of an otherwise identical control cell (e.g., the same cell but without an inactivated propionyl-CoA carboxylase gene) that is able to convert propionyl-CoA into methylmalonyl-CoA. In particular cases, methylmalonyl-CoA may be undetectable in the cell. In certain cases such a cell, without any of the additional enzymes discussed below, may contain an increased level of propionyl-CoA relative to a cell that is able to convert propionyl-CoA to methylmalonyl-CoA. In certain cases, in the absence of the additional enzymes discussed below, a subject cell may contain at least 5 times more, at least 10 times more, at least 50 times more, at least 100 times more, or at least 1,000 times or more propionyl-CoA relative to an otherwise identical cell that is able to convert propionyl-CoA to methylmalonyl-CoA, when grown in a medium containing an odd numbered chain alkane. Propionyl-CoA accumulation may be detected by the accumulation of propionate.

Figure 2:
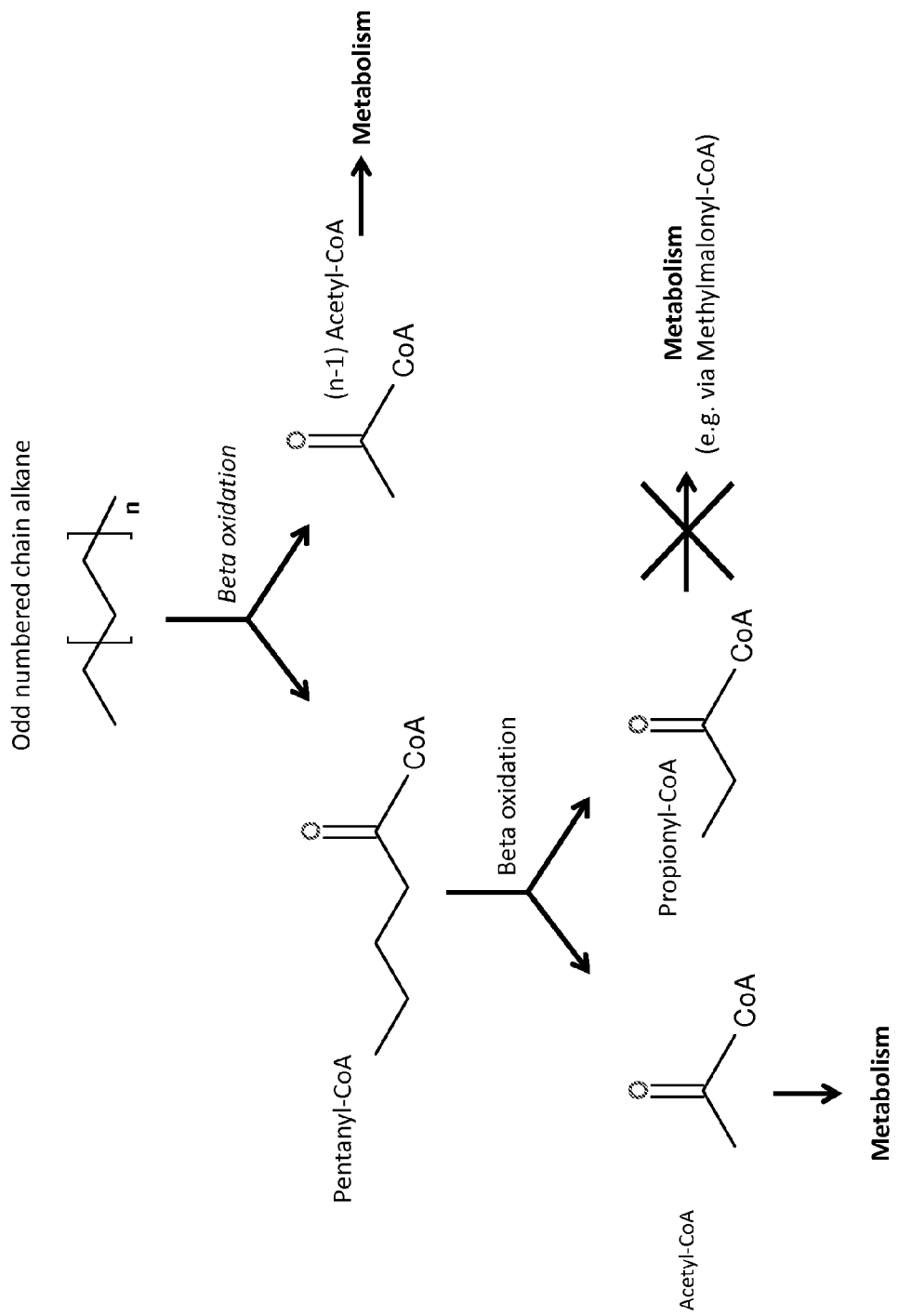
FIG. 2 shows an exemplary biochemical pathway for how odd-numbered chain alkanes may be metabolized by β-oxidation in a cell that is unable to convert propionyl-CoA into methylmalonyl-CoA. The propionyl-CoA (or, as will be described in greater detail below, 5-hydroxypropionyl CoA) is used to make acrylate or a precursor for the same (e.g., propionate, 3-hydroxypropionyl-CoA, 3-hydroxypropionate, acrylyl-CoA).

FIG. 2 generally illustrates one embodiment of how an odd-numbered alkane may be metabolized in a cell that is unable able to convert propionyl-CoA to methylmalonyl-CoA. In this example, the lack of a propionyl-CoA carboxylase or 2-methylcitrate synthase enzyme leads to an increase in the amount of propionyl-CoA. As will be described in greater detail below (and depending upon which other enzymes are present in the cell), such a cell can produce acrylate or a precursor for the same (e.g., propionate, 3-hydroxypropionyl-CoA, 3-hydroxypropionate, or acrylyl-CoA) that can be readily converted to acrylate enzymatically or by chemical treatment, when the cell is grown on an odd numbered chain alkane.

Production of 3-hydroxypropionyl-CoA

In one embodiment illustrated in FIG. 3, a cell may be modified to contain a hydroxylase enzyme that has any one or more of the following activities: a) an ability to hydroxylate an alkane at the omega position to produce an omega-hydroxyalkane, (e.g., an ability to convert pentane to 5-hydroxypentane, where the omega carbon is hydroxylated and the unhydroxylated end is later hydroxylated and oxidized by β-oxidation); b) the ability to hydroxylate an alkanoic acid at the omega position to produce omega-hydroxyalkanoic acid (e.g., an ability to convert pentanoic acid to 5-hydroxypentanoic acid); c) an ability to convert pentanyl-CoA into 5-hydroxypentanyl CoA; and/or d) an ability to convert propionyl-CoA to 3-hydroxypropionyl CoA. A single enzyme may have all of these activities, or a single enzyme may have one or more but not all of the activities. Using pentane as an example (as illustrated in FIG. 3), the hydroxylase may be non-specific in that it can hydroxylate any of the substrates at the asterisk (shown in FIG. 3), or specific in that it can hydroxylate only 1, 2 or 3 substrates at the asterisk shown in FIG. 3. If pentane is used as a feedstock, the hydroxylase may hydroxylate the omega position of pentane, pentanoic acid, pentanyl CoA or propionyl-CoA. As will be discussed below, the enzyme may in certain cases be engineered to increase or decrease its ability to hydroxylate any one or more of these substrates. If a longer odd numbered chain alkane is used as a feedstock, the enzyme may hydroxylate pentanoyl-CoA, propionyl-CoA, any of the longer chain precursors of those molecules that are made during β-oxidation, or the longer odd numbered chain alkane. Again, the enzyme may in certain cases be engineered to increase or decrease its ability to hydroxylate any one or more of these substrates.

As illustrated in FIG. 3, hydroxylation of any of the substrates at the asterisk will result in the production of 3-hydroxypropionyl-CoA, which can be readily converted to 3-hydroxypropionate enzymatically (for example, by enzymes of family EC 3.1.2.4 or similar functionality) or by chemical treatment (for example, exposure to a strong acid or base). These downstream steps may be done enzymatically (either in the cell, or by addition of an isolated enzyme to a cell lysate) or by chemical treatment of a cell lysate.

In this embodiment, the cells are characterized in that they produce 3-hydroxypropionyl-CoA. In particular embodiments, particularly those in which the cell comprises a 3-hydroxypropionyl-CoA hydrolase or 3-hydroxypropionyl-CoA transferase, the cell may additionally contain 3-hydroxypropionic acid.

Once made, the 3-hydroxypropionic acid can be dehydrated to produce acrylic acid. This step can also be done enzymatically in a cell or by dehydration by distillation, methods for which are known. The acrylic acid can be conveniently packaged, shipped, and used in a variety of manufacturing processes, as described above.

In particular embodiments, the hydroxylase in the cell may be wild-type. In these embodiments, the hydroxylase may be a wild-type hydroxylase from a different species to the subject host cell (i.e., a wild type hydroxylase that is non-native to the host cell). Alternatively, the propionyl-CoA carboxylase gene may be inactivated in a cell that already contains a suitable wild-type hydroxylase, in which case the wild-type hydroxylase will be native to the host cell.

In other embodiments discussed, the hydroxylase may be a variant of a wild-type enzyme.

In certain embodiments, the hydroxylase may be a wild-type or modified cytochrome P450 or alkane oxidase enzyme. The biochemistry, structure/function relationships, conserved domains and active sites of such enzymes are known in the art. In particular embodiments, the amino acid sequence of the hydroxylase may have at least 70% sequence identity (e.g., at least 80% sequence identity, at least 85% sequence identity, at least 90% sequence identity, at least 95% sequence identity or at least 97% sequence identity) to the amino acid sequence of a cytochrome P450 enzyme listed in Table 1 below.

TABLE 1

| Enzyme name | GI | Species |
|---|---|---|
| CYP4A | 28460698 | Mammalian |
| CYP4B | 126722981 | Mammalian |
| CYP4B1 | 126722981 | Rabbit |
| CYP4V2 | 39841339 | *Homo sapiens* |
| CYP86A22 | 71726941 | *Petunia* hybrid |
| CYP94A4 | 332189189 | *Arabidopsis thaliana* |
| CYP97B3 | 240255695 | *Arabidopsis thaliana* |
| CYP52A21 | 3395458 | *Candida albicans* |
| CYP52A9 | 442497 (partial) | *Candida maltose* |
| CYP52A10 | 218357 | *Candida maltose* |
| CYP52A11 | 218358 | *Candida maltose* |
| CYP52A13 | 29469865 | *Candida tropicalis* |
| CYP52A17 | 29469875 | *Candida tropicalis* |
| CYP52A12 | 223590183 | *Debaryomyces hansenii* |
| CYP52A13 | 18203639 | *Debaryomyces hansenii* |
| CYP52F1 through F11 | | *Yarrowia lipolytica* |
| CYP52F1 | 3298288 | *Yarrowia lipolytica* |
| CYP52F2 | 3298290 | *Yarrowia lipolytica* |
| CYP52F3 | 3298292 | *Yarrowia lipolytica* |
| CYP52F4 | 3298294 | *Yarrowia lipolytica* |
| CYP52F5 | 3298296 | *Yarrowia lipolytica* |
| CYP52F6 | 3298298 | *Yarrowia lipolytica* |
| CYP52F7 | 3298300 | *Yarrowia lipolytica* |
| CYP52F8 | 3298302 | *Yarrowia lipolytica* |
| CYP52F9 | 49646138 | *Yarrowia lipolytica* |
| CYP52F10 | 49646426 | *Yarrowia lipolytica* |
| CYP52F11 | 49647014 | *Yarrowia lipolytica* |
| CYP153A6 | 51997117 | *Mycobacterium* sp. HXN-1500 |
| CYP153 | 13940008 | *Acinetobacter* sp. EB104 |
| CYP153A16 | 183983152 | *Mycobacterium marinum* |
| CYP153A | 91791108 | *Polaromonas* sp. |

Production of acrylyl-CoA

Figure 4:
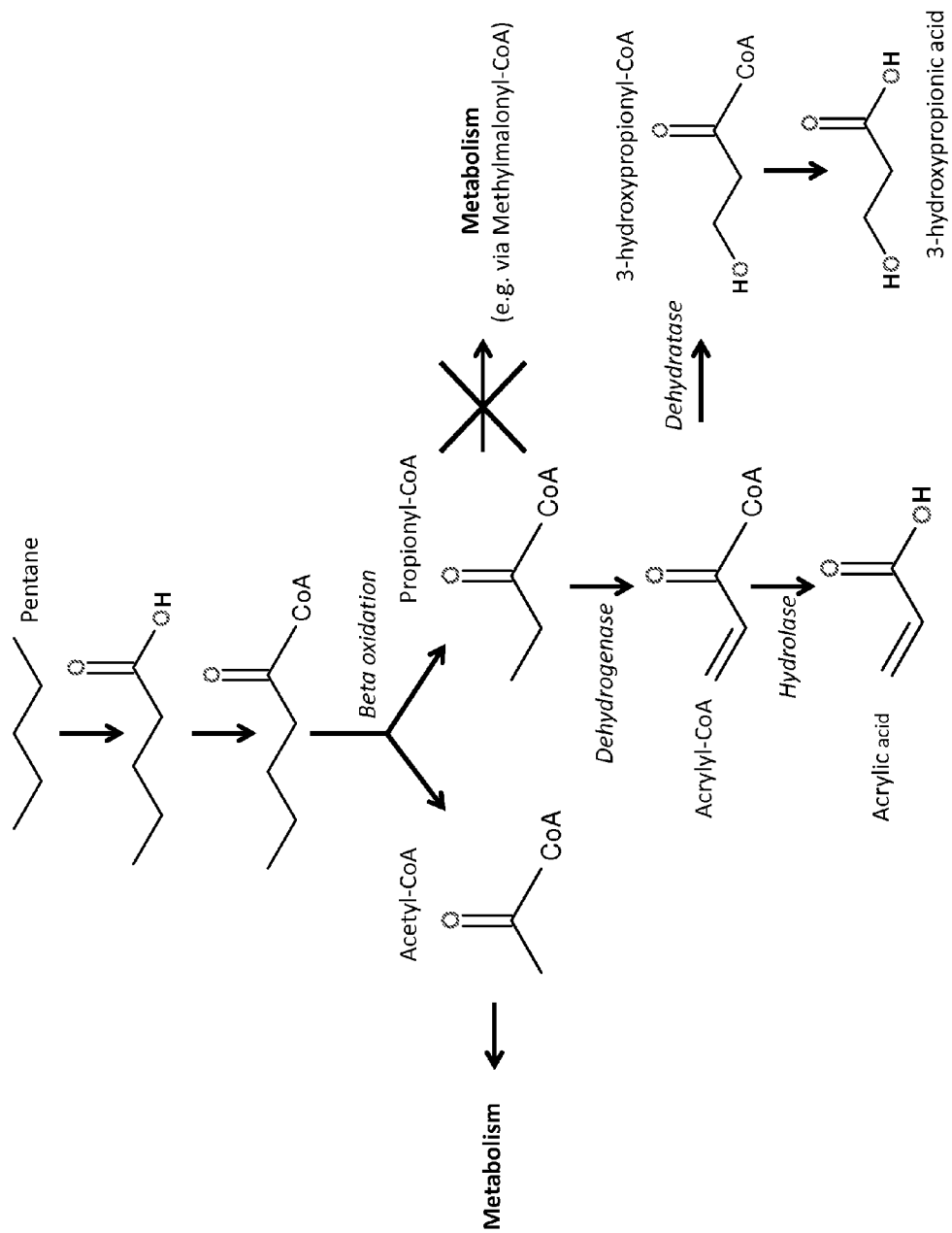
FIG. 4 shows a biochemical pathway describing how acrylyl-CoA, acrylate and other precursors of acrylate can be made in a subject cell. This exemplary pathway uses pentane as a feedstock, although other odd-numbered chain alkanes may be used.

In an alternative embodiment shown in FIG. 4, the host cell may comprise an acyl-CoA oxidase/dehydrogenase such as propionyl-CoA dehydrogenase enzyme capable of converting propionyl-CoA to acrylyl-CoA. Propionyl-CoA dehydrogenase is a known enzyme described in, e.g., Zhou et al (*Expression and Characterization of a Novel Propionyl-CoA Dehydrogenase Gene from Candida rugosa in Pichia pastoris*. Appl Biochem Biotechnol. 2011 Sep. 30; Epub ahead of print); Zhou et al (*Cloning and transcription analysis of the Candida rugosa propionyl-CoA dehydrogenase gene and its expression in Pichia pastoris*. J. Basic Microbiol. 2011 Jul. 21; Epub ahead of print); Hasan (Appl. Environ. Microbiol. 2011 77:572-9; Hetzel et al (Eur. J. Biochem. 2003 270:902-10) Fernández-Briera et al (Biochimie 1988 70:757-68) and Lloyd et al (Biochem J. 1967 104:639-46). In one embodiment, the propionyl-CoA dehydrogenase may be a wild-type or variant version of a wild-type propionyl-CoA dehydrogenase such as that defined by Genbank accession no. XP_503244.1, which provides the amino acid sequence of a propionyl-CoA dehydrogenase from *Y. lipolytica*. Orthologs of this gene from other species are readily identifiable using bioinformatics or routine molecular techniques. Related wild type sequences include those defined by Genbank accession nos. XP_001385628 (*Scheffersomyces stipitis*), GU338397.1 (*Candida rugosa*), YP_002784373 (*Rhodococcus opacus*) and AF_241171 (*Pseudomonas aeruginosa*), NP_000007.1 (*Homo sapiens*), NP_999204.1 (*Sus scrofa*) for example. In this embodiment, the cells are characterized in that they produce acrylyl-CoA. Again, the enzyme may be wild type and native to the host cell, or wild-type and non-native to the host cell. In particular embodiments, the enzyme may be a variant of a wild type protein, as discussed below.

One made in a cell, the acrylyl-CoA can be readily hydrolyzed to acrylate, either enzymatically (using an acrylyl-CoA hydrolase or acrylyl-CoA transferase) or by treatment with a base. These steps may be done enzymatically (either in the cell, or by addition of an isolated enzyme to a cell lysate) or by treatment of a cell lysate with a base. Cells that can hydrolyze acrylyl-CoA are characterized in that that they produce acrylate.

As an alternative to being used to producing acrylate, the acrylyl may be dehydrated to produce 3-hydroxypropionyl-CoA. In these embodiments, the cell may further comprises a 3-hydroxypropionyl-CoA dehydratase enzyme that converts the acrylyl-CoA to 3-hydroxypropionyl-CoA. This enzyme activity (defined by the activity EC 4.2.1.116) has been described in a variety of publications (see, e.g., Teufel J. Bacteriol. 2009 191:4572-81; Fitzsimmons et al Biochemistry 1995 34:4276-86; and D'Ordine Biochemistry. 1994 33:14733-42). Amino acid sequences for such an enzyme are provided by, e.g., Genbank accession nos. 322518307 (*Metallosphaera sedula*), 342306520 (*Sulfolobus tokodaii*); 330834150 (*Metallosphaera cuprina*) and 148569418 *Roseiflexus* sp.). Orthologs of these sequences from other species are readily identifiable using bioinformatics or routine molecular techniques. These cells may be characterized in that they produce 3-hydroxypropionyl-CoA. The 3-hydroxypropionyl-CoA can be converted to 3-hydroxypropionate using any of the methods described above.

Figure 5:
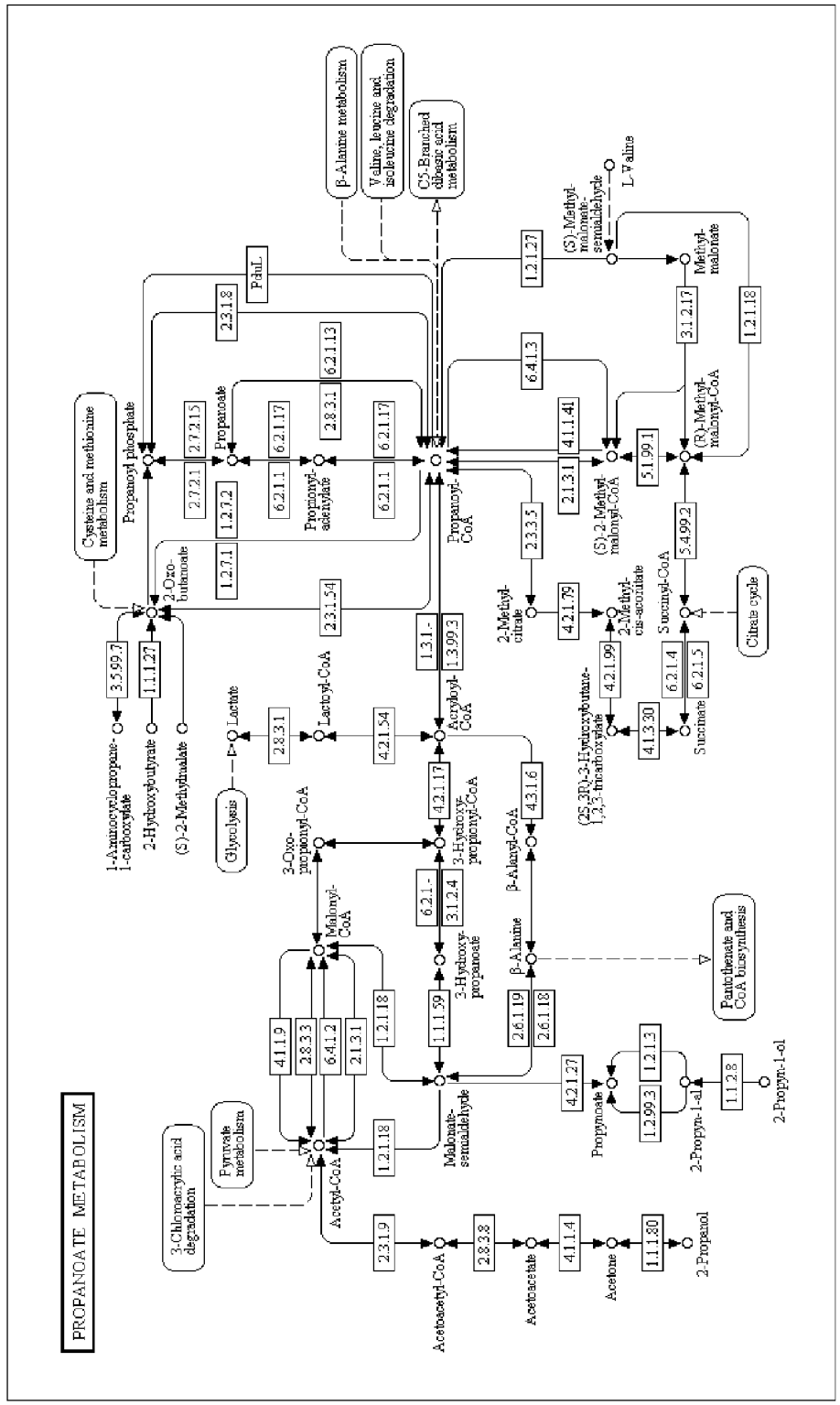
FIG. 5 shows how various enzymes contribute to propionate metabolism.

In either of the embodiments described above (i.e., regardless of whether the host cell produces acrylyl-CoA or 3-hydroxypropionyl-CoA), the cell may further comprise one or more of the following modifications: an inactivated 3-hydroxyisobutyrate dehydrogenase gene, an inactivated aldehyde dehydrogenase gene, an inactivated acetyl-CoA carboxylase gene, an inactivate malonyl-CoA reductase gene, an inactivated 3-hydroxypropionyl-CoA dehydratase gene, or an inactivated lactyl-CoA dehydratase gene. FIG. 5 illustrates how these and other genes contribute to propionate metabolism. In addition, in certain cases, the host cell may further contain a membrane transporter for importing alkane (e.g., pentane) into the host cell and for exporting the 3-hydroxypropionate out of the host cell. Many host cells have these transporters already.

Methods for expressing recombinant proteins in many different species are known and need not be discussed in any detail. Guidance for the production of expression vectors and protein production in a variety of host cells is provided in Sambrook et al., 2001, Molecular Cloning: A Laboratory Manual, 3rd d Ed., Cold Spring Harbor Laboratory Press; and Current Protocols in Molecular Biology, Ausubel, Greene Pub. Associates, 1998, updates to 2006.

Production of 3-hydroxypropionate

In an alternative embodiment shown in FIG. 4, the host cell may comprise an enzyme capable of converting 3-hydroxypropionyl-CoA into 3-hydroxypropionate. Enzymes in the family of EC 3.1.2.4 with hydrolase activities may be used to catalyze this reaction. In one embodiment, the hydrolase may be a wild-type or variant version of a wild-type 3-hydroxyisobutyryl-CoA hydrolase such as defined by Genbank accession nos. NP_055177.2 (*Homo sapiens*); NP_001013100.1 (*Mus musculus*). Enzymes in the family of EC 6.2.1.1 with synthetase/ligase activities may also be used to catalyze this reaction. In one embodiment, the hydrolase maybe a wild-type or variant version of a wild-type acetyl-CoA synthetase such as defined by Genbank accession nos XP_505057.1 (*Y. lipolytica*); XP_002547725.1 (*C. tropicalis*), XP_002550431.1 (*C. tropicalis*). NP_009347.1 (*S. cerevisiae*).

Enzyme Variants

In any of the embodiments described above, a particular enzyme may be native to the host cell, or not native to the host cell. Additionally, the enzyme may be a wild type enzyme or may be a variant of a wild-type enzyme, where a variant of an enzyme may have an amino acid sequence that is at least 70% sequence identical (e.g., at least 80% identical, at least 85% identical, at least 90% identical, at least 95% identical or at least 97% identical) to the amino acid sequence of a wild type wild type enzyme. Since many of the enzymes described above have been described structure and functionally, and because the amino acids of such enzymes from many different species are available, the production of active variants should be routine.

In particular embodiments, the amino acid sequence of an enzyme may be optimized for the reaction in which it is being used, e.g., to increase its specificity for a substrate or to increase the reaction rate for a particular substrate, etc. In a particular embodiment, the amino acid sequence of the hydroxylase enzyme described above may be optimized to perform any one or more of the following activities: a) the ability to hydroxylate an alkane at the omega position to produce an omega-hydroxyalkanoic acid, e.g., the ability to convert pentane to 5-hydroxypentane; b) the ability to hydroxylate an alkanoic acid at the omega position to produce omega-hydroxyalkanoic acid, e.g., the ability to convert pentanoic acid to 5-hydroxypentanoic acid; c) the ability to convert pentanoyl-CoA into 5'-hydroxypentanyl CoA; and/or d) the ability to convert propionyl-CoA to 3-hydroxypropionyl CoA.

Methods for engineering enzymes are known and include: mutagenesis and/or DNA shuffling as described in Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, Nat. Biotechnol 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). In particular cases, such variants may be designed using the phylogenetic-based methods described in, for example, U.S. Pat. No. 8,005,620 and Gustafsson (Curr. Opin. Biotechnol. 2003 14:366-70; which are incorporated by reference for disclosure of such methods) as well as Welch et al (J. R. Soc. Interface. 2009 6: S467-76), Villalobos et al (BMC Bioinformatics 2006 7: 285) Minshull et al (Curr Opin Chem Biol. 2005 9:202-9), Gustafsson et al (Trends Biotechnol. 2004 22:346-53) and Minshull (Methods 2004 32:416-27).

In one embodiment, a hydroxylase e.g., a cytochrome P450 or alkane oxidase, that can hydroxylate the omega position of a long chain alkane or a long chain betaoxidation product of the same, may be modified to make it more active on shorter substrates, e.g., those shown in FIG. 3.

Cell Cultures and Culture Methods.

Also provided is a cell culture comprising: a) a culture medium comprising an odd-numbered chain alkane (e.g., heptane, pentane or propane); and b) a population of the above-described cells, wherein said cell culture is characterized in that it contains 3-hydroxypropionyl CoA or acrylyl-CoA (where use of the term "or", unless otherwise indicated, does not exclude the other compound from being present), depending upon whether the cells contain an enzyme that can hydroxylate the omega carbon of an alkane or a β-oxidation product of the same, or a propionyl-CoA dehydrogenase. In particular embodiment, the culture medium may comprise a mixture of different alkanes, e.g., a feedstock that contains at least 50% of several different odd numbered chain alkanes.

The cell culture may be maintained under conditions suitable for growth of the cells, thereby producing 3-hydroxypropionyl CoA or acrylyl-CoA. As noted above, the 3-hydroxypropionyl-CoA or acrylyl-CoA may not be the final product and, as such, those products may be converted into other by-products before being harvested. In a particular embodiment, the 3-hydroxypropionyl CoA or acrylyl-CoA from may be harvested from the cell culture and used to make 3-hydroxypropionate or acrylate, respectively, as described above. In other embodiments, a lysate of the cells may be treated with a base to produce 3-hydroxypropionate or acrylate, respectively. Likewise, if the cells make 3-hydroxypropionate, a lysate of the cells (or the culture medium if the 3-hydroxypropionate is secreted) may be readily converted to acrylate by chemical treatment. The acrylic acid can be conveniently packaged, shipped, and used in a variety of manufacturing processes, as described above.

In order to further illustrate the present invention, the following specific examples are given with the understanding that they are being offered to illustrate the present invention and should not be construed in any way as limiting its scope.

EXAMPLE 1

Selection of Strains with High 3-hydroxypropionate Tolerance

Figure 6:
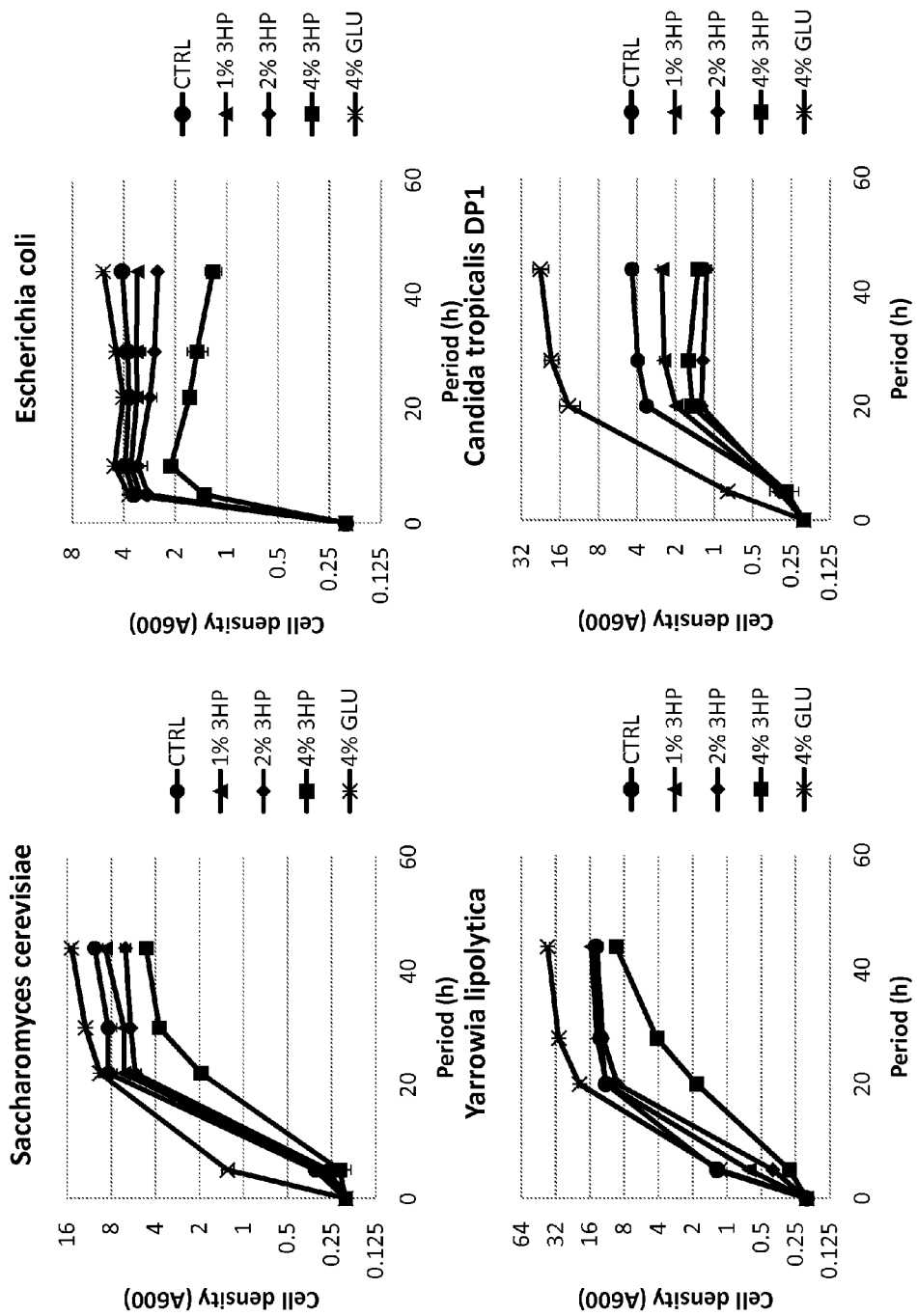
FIG. 6 is a panel of four graphs showing that *Y. lipolytica* exhibits higher tolerance to 3-HP then other microorganisms.

Certain organic acids, including 3-HP, can be toxic to many microorganisms, e.g., *Escherichia coli*, at concentrations well below those which are required for economical production. Further, it has been reported that organic acids inhibit microbial growth by lowering the pH of fermentation media. Organic acids may also exert toxicity by anion-specific effects on metabolism. For this reason, it is desirable to utilize microorganisms that exhibit natural high organic acid tolerance that can be engineered for production of acrylate precursor chemicals. To select for a suitable microorganisms for acrylate precursor production, the growth of *Candida tropicalis* DP1, *Yarrowia lipolytica*, *Saccharomyces cerevisiae* ATCC 4132, and *Escherichia coli* BL21 was tested in their respective optimal growth media and in the presence of 3-HP. Patched colonies on agar plates were used to inoculate 3-mL liquid rich media (Yeast Peptone Dextrose (YPD) medium for *C. tropicalis*, *Y. lipolytica* and *S. cerevisiae*, and Luria Broth (LB) for *E. coli*). The cultures were grown for ~24 h aerobically at 25-28° C. This preinoculum was then used to seed 1 mL media at a starting cell density ($A_{600\ nm}$) of 0.2. 3-HP was added into the media at concentrations ranging from 1% to 4%, and the microorganisms were cultured aerobically at 25-28° C. for 50 h. As shown in FIG. 6, *Y. lipolytica* exhibits higher tolerance in culture containing up to 4% 3-HP over the commonly used industrial microorganisms such as *Escherichia coli* and *Saccharomyces cerevisiae*. After 50 h growth in the presence of 4% 3-HP, *Y. lipolytica* achieved $A_{600\ nm}$ up to ~8, whereas *C. tropicalis*, *S. cerevisiae* and *E. coli* only achieved an $A_{600\ nm}$ of ~1, ~4 and ~1, respectively.

EXAMPLE 2

Metabolic Engineering for Increased Propionyl-CoA, the Committed Precursor of 3-HP Synthesis from Odd-Numbered Alkanes The assimilation of odd-numbered alkanes such as pentane leads to the formation of metabolites, namely acetyl-CoA and propionyl-CoA. While acetyl-CoA is metabolized further to support growth and biomass generation, propionyl-CoA can be harnessed as a substrate for the production of intermediates in acrylate biosynthetic pathways. Under typical growth conditions, however, intracellular propionyl-CoA levels can be low because they may be metabolized by one or more of three possible pathways. In the first pathway, propionyl-CoA may be converted into methylmalonyl-CoA by the enzyme propionyl-CoA carboxylase (encoded by the gene ppc). In the second pathway, propionyl-CoA may be converted into 2-methylcitrate by the enzyme 2-methylcitrate synthase (encoded by the gene prpC). These two pathways eventually enter central carbon metabolism to support growth. In the third pathway, propionyl-CoA is converted into propionate by the action of propionyl-CoA: succinatetransferase and propionyl-CoA kinase.

To create a strain suitable for production of acrylate or acrylate intermediates from odd-numbered alkanes, the alkane-assimilating microorganism *Yarrowia lipolytica* was engineered to reduce its ability to assimilate propionyl-CoA. The genetic loci containing ppc and prpC genes were deleted in order to inactivate propionyl-CoA carboxylase and 2-methylcitrate synthase, respectively. The nucleotide sequences of the deletion cassettes are shown in SEQ ID NOS 1 and 2. The first and last 61 nucleotides of SEQ ID NO:1 and the first 68 and last 63 nucleotides of SEQ ID NO:2 are the homologous sequence outside of the 5'- and 3'-end of the target gene deletion. For ppc deletion, the deletion cassette contained a 61-bp fragment homologous to the 5'-flanking region and also a 61-bp fragment homologous to the 3'-flanking region of ppc. Similarly for prpC deletion, the deletion cassette contained a 68-bp fragment homologous to the 5'-flanking region and 61-bp fragment homologous to the 3'-flanking region of prpC. In both deletion cassettes, the 5'- and 3'-homologous segments flanked a selectable gene marker encoding the *Y. lipolytica* beta-isopropylmalate dehydrogenase (LEU2) and its native promoter and terminator sequence. In all cases, the deletion cassettes were assembled de novo (DNA2.0). Custom oligonucleotides (primers) were then used to amplify the cassettes with PCR using Pfx polymerase (Invitrogen) with the following reaction conditions: 1 cycle of 95° C. for 2 mins followed by 30 cycles of 95° C. for 30 secs, 58° C. for 30 secs, 68° C. for 4.5 mins, and followed by 72° C. for 1 min. The deletion cassettes were then introduced into *Y. lipolytica* POf1 strain (MATA ura3-302 leu2-270 xpr2-322 axp2-deltaNU49 XPR2::SUC2) (ATCC MYA-2613) using electroporation or chemical transformation using Frozen-EZ yeast transformation (Zymo Research). Successful recombination events were selected by growth on media lacking leucine, as complementation of leucine auxotrophy is conferred by the LEU2 marker gene. Several *Y. lipolytica* colonies that were able to grow on CM minimal media plus glucose minus leucine (Teknova) were isolated. Further, genomic DNA of these colonies was extracted and subjected to PCR analysis according to Gussow et al. Direct Clone Characterization from Plaques and Colonies by the Polymerase Chain Reaction. Nucleic, Acids Res. 17, 1989, 4000 for determination of positive chromosomal gene deletion.

Figure 7:
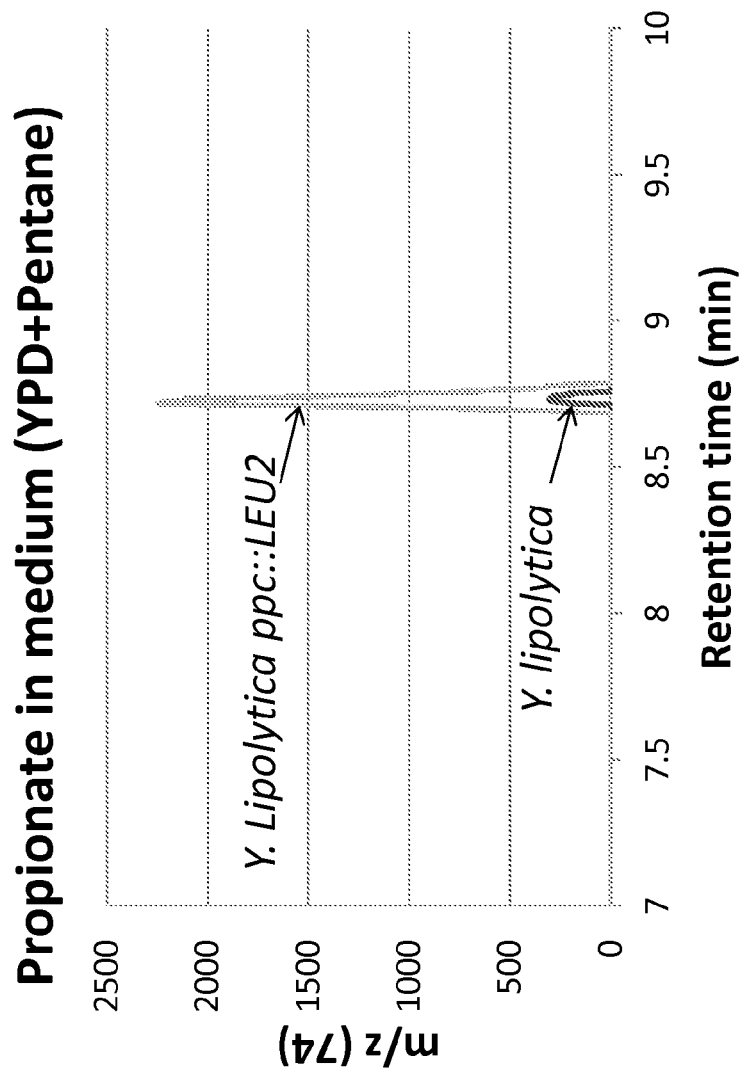
FIG. 7 shows the results of a GC/MS analysis of culture medium.
Figure 8:
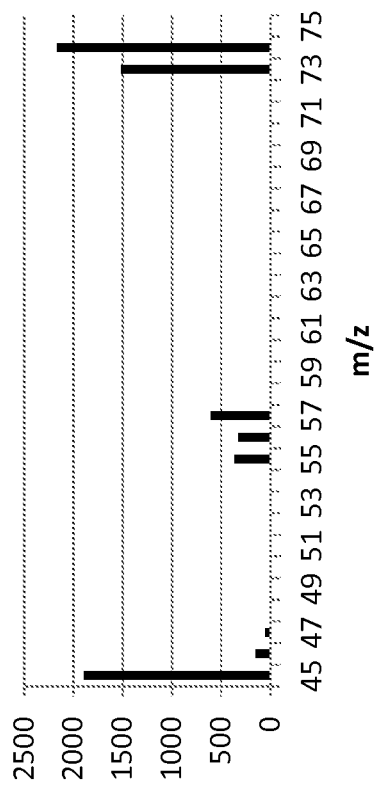
FIG. 8 shows two graphs that show that the GC/MS fragmentation pattern of propionate produced by *Y. lipolytica* ppc::LEU2 mutant in the presence of pentane matches the authentic standard of propionic acid (purchased from Sigma).
Figure 8:
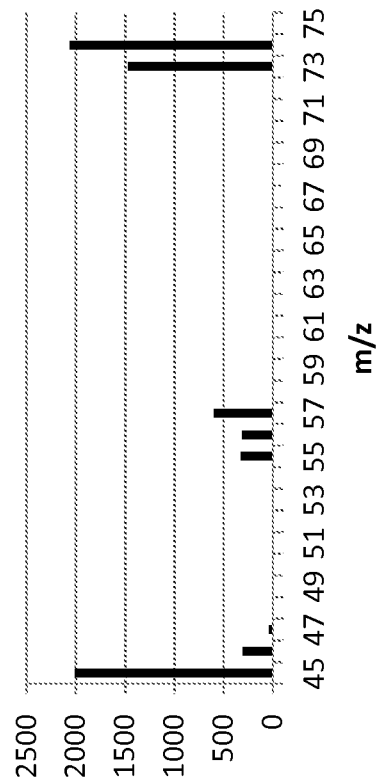

To verify the capability of the cells to perform biotransformation of alkanes, individual colonies of ppc::LEU2 and prpC::LEU2 were first patched onto yeast extract, peptone, and dextrose (YPD) agar plates (Teknova), and incubated overnight at 25-28 C. The colonies were then cultured aerobically at 25-28° C. in liquid media in the presence of 1% (v/v) pentane. Propionate accumulation in the culture media was assessed using a GC/MS method. Specifically, the culture media was acidified by addition of HCl or glacial acetic acid to convert dissolved propionate to propionic acid. Propionic acid was then extracted into an equal volume of methylene chloride and detected by analysis on a GC/MS (Hewlett Packard 6890 GC/5972 MSD). One microliter of organic phase was injected onto an HP Agilent J&W DB-FFAP column (30 m length×0.25 mm i.d.×0.25 µm film, oven program 90° C. 5 min, 10° C. min-1 to 140° C., 25° C. min-1 to 240° C., 240° C. 6 min). Peak integration was compared to a reference using purified propionic acid standards for quantification. The parent POf1 strain was used as a negative control to assess increased propionate production by the ppc::LEU2 and prpC::LEU2 mutants. As shown in FIG. 7, GC/MS analysis of the culture medium showed that in the presence of pentane, propionate concentration in the culture medium of mutant POf1 carrying ppc::LEU2 mutation increased up-to ~7 fold when compared to the parent POf1 strain at 24 h. On the other hand, propionate level in the culture medium of prpC::LEU2 mutant did not increase when compared to that of the POf1. As shown in FIG. 8, the GC/MS fragmentation pattern of propionate produced by *Y. lipolytica* ppc::LEU2 mutant in the presence of pentane (biotransformation) matches the authentic standard of propionic acid (Sigma).

EXAMPLE 3

Figure 9:
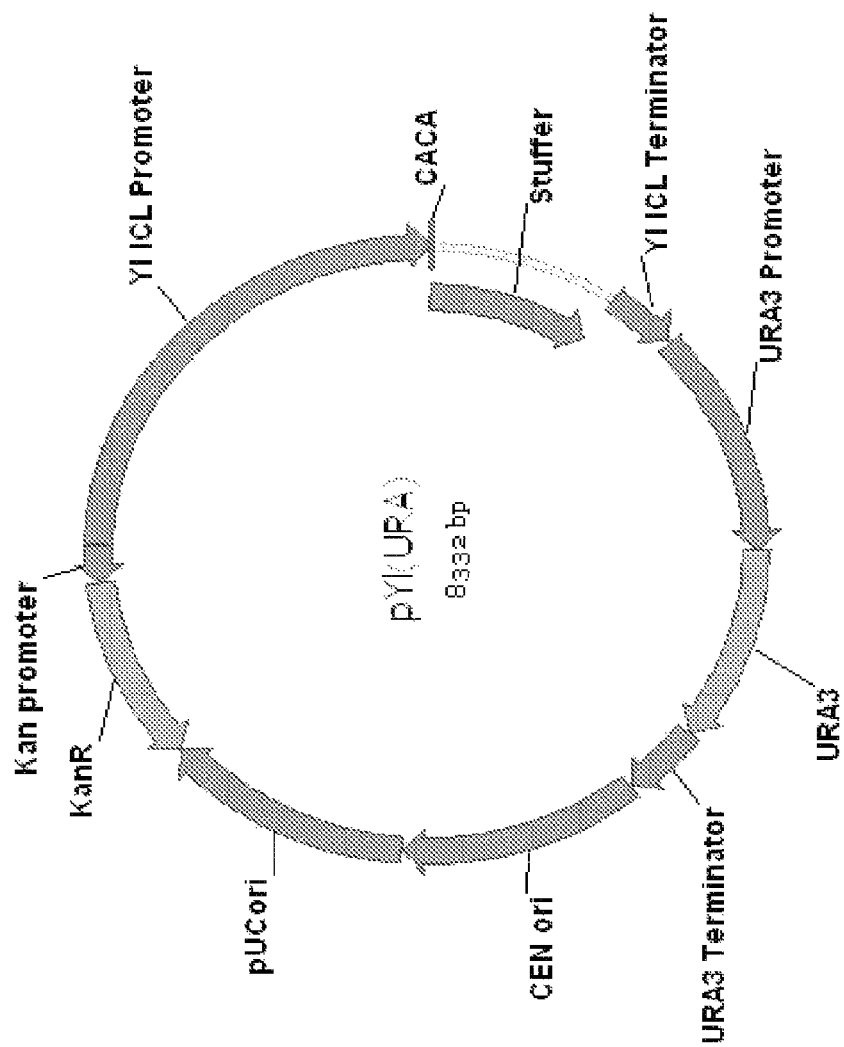
FIG. 9 shows a map of expression vector pYL(Ura).
Figure 10:
FIG. 10 shows that expression of Dasher in *Y. lipolytica* POf1 transformants carrying pYL(Ura)+Dasher conferred green fluorescent coloration when compared to the host strain.

Construction of Vector DNA for Heterologous Protein and Pathway Expression in Alkane-Assimilating Microorganisms The engineered strain with increased propionyl-CoA can be used as a suitable host for production of value-added chemicals, such as acrylate. For this purpose a synthetic pathway containing one or multiple biosynthetic enzymes (wild-type and/or heterologously derived and/or their variants) can be functionally expressed in the host. Suitable enzymes to enable acrylate production are for example, cytochrome P450, alkane oxidase, acyl-CoA oxidase, enoyl-CoA hydratase, and hydrolase. For the purpose of enabling protein and pathway expression in a suitable acrylate-producing host such as *Y. lipolytica* ppc::LEU2 mutant, we synthesized a new expression vector pYL(Ura) (DNA2.0) (shown in FIG. 9) that includes genetic elements that encode for a kanamycin resistance gene marker, a bacterial replicon (pUCori), a *Y. lipolytica* CEN replicon for autonomous replication, *Y. lipolytica* URA3 (orotidine-5'phosphate decarboxylase) gene marker, and *Y. lipolytica* isocitrate lyase (ICL) promoter for expression of heterologous protein, and a stuffer region containing multiple cloning sites for insertion of DNA sequences that encode for a protein of interest. A demonstration of the functional expression of a protein in *Y. lipolytica* using this vector for example is the use of a green-colored fluorescent protein (Dasher). The gene that encodes for this protein was inserted in between NcoI and NotI cloning sites of pYL(Ura) to create pYL(Ura)+Dasher. The gene (SEQ ID NO: 3) was synthetically constructed (DNA2.0) with altered nucleotide sequence to match the codon bias in *Y. lipolytica*. As shown in FIG. 10, expression of Dasher in *Y. lipolytica* POf1 transformants carrying pYL(Ura)+Dasher conferred green fluorescent coloration when compared to the host strain.

EXAMPLE 4

Engineering 3-HP Biosynthesis from Odd-Numbered Alkanes in Mutant Strain Accumulating Propionyl-CoA To enable 3-HP production from odd-numbered alkanes, a synthetic pathway is engineered into propionyl-CoA accumulating strains, for example, *Y. lipolytica* ppc::LEU2. In one instance, an engineered pathway simultaneously expresses a ω-cytochrome P450 and a hydrolase. In this case, intracellular propionyl-CoA is first converted into 3-hydroxypropionyl-CoA (3-HP-CoA). The subsequent CoA cleavage by the hydrolase enzyme yields 3-HP. In another instance, the engineered pathway simultaneously expresses acyl-CoA oxidase, enoyl-CoA hydratase, and hydrolase. In this case, intracellular propionyl-CoA is first converted into acrylyl-CoA. Subsequently, acrylyl-CoA is converted into 3-HP-CoA. CoA-cleavage of 3-HP-CoA yields 3-HP. In order to obtain a highly functional pathway, pathway variants comprising genes from various origins using a combinatorial approach were constructed. For example, a two-enzyme pathway whereby five gene sequences are used for each gene yields a total of 25 pathway variants. The expression of each enzyme in a single cassette is modulated independently using either the isocitrate lyase (ICL) or the translation elongation factor (TEF) promoter. In all cases, all cassettes are synthesized de novo (DNA2.0) prior cloning into pYL(Ura). pYL(Ura) containing the combinatorial-enzyme cassettes are then transformed into *Y. lipolytica* ppc::LEU2. Positive transformants are then selected on CM minimal media plus glucose minus leucine and uracil (Teknova). Individual colonies are first patched onto YPD agar plates (Teknova), and incubated overnight at 25-28° C. The colonies were then cultured aerobically at 25-28° C. in liquid media in the presence of alkanes, for example, 1% (v/v) pentane. 3-HP production by the engineered strains are quantified by analyzing the culture media using a GC/MS method. Specifically, the culture media (where one would expect the 3-HP) are acidified by addition of HCl or glacial acetic acid. 3-HP is then extracted into an equal volume methylene chloride. Extracted 3-HP is detected by analysis on a GC/MS (Hewlett Packard 6890 GC/5972 MSD). One microliter of organic phase is injected onto HP Agilent J&W DB-FFAP column (30 m length×0.25 mm i.d.×0.25 µm film, oven program 90° C. 5 min, 10° C. min-1 to 140° C., 25° C. min-1 to 240° C., 240° C. 6 min). Peak integration is compared to the reference using authentic compound for quantification.

EXAMPLE 5

Production of Acrylate from Alkanes in *Candida tropicalis*

To create an additional yeast strain suitable for production of acrylate or acrylate from odd-numbered alkanes, the alkane-assimilating microorganism *Candida tropicalis* is first metabolically engineered for improvement of acrylyl-CoA content. Subsequently, a short-chained acyl-CoA thioesterase/hydrolase encoding enzyme is introduced into the host strain. With this strategy, the genes that encode for an acyl-CoA dehydrogenase with propionyl-CoA dehydrogenase activity (CTRG_05958) and hydrolase are custom synthesized (DNA2.0) and cloned independently such that the expression of CTRG_05958 is modulated by the *C. tropicalis* isocitrate lyase (ICL) promoter; whereas the hydrolase expression is modulated by the pyruvate dehydrogenase (PDC) promoter. The integration vector pCT (HygR) containing a hygromycin resistance gene marker (DNA2.0) is used to assemble the construct. Subsequently, for chromosomal insertion of the gene construct into the chromosome, the integration vector containing the two genes is linearized by the restriction enzyme that recognizes a unique restriction site within the ICL promoter fragment. Approximately two µg of linearized DNA is introduced into *C. tropicalis* using electroporation. Successful recombination events are selected by growth on YPD agar containing 200 µg/mL hygromycin (YPDH). *C. tropicalis* transformants able to grow well on YPDH are isolated. Genomic DNA of these colonies is extracted and subjected to PCR analysis according to Gussow et al. Direct Clone Characterization from Plaques and Colonies by the Polymerase Chain Reaction. Nucleic, Acids Res. 17, 1989, 4000 for determination of positive chromosomal gene integration.

To verify the capability of the recombinant cells to perform biotransformation of alkanes, individual colonies are first patched onto YPDH agar plate, and incubated overnight at 30° C. The colonies are then cultured aerobically for 24 h at 30° C. in liquid growth medium containing 390 mL of 1% yeast extract and 2% peptone, 50 mL of 1M phosphate, 50 mL of 10× Yeast Nitrogen Base solution, and 10 mL 50% glycerol. Subsequently, the cells are pelleted and resuspended in the biotransformation/induction medium containing 394.8 mL of 1% yeast extract and 2% peptone, 50 mL of 1M phosphate, 50 mL of 10× Yeast Nitrogen Base solution, 5.2 mL of ethanol, and 1% (v/v) pentane. Acrylate accumulation in the culture media is assessed using a GC/MS method. Specifically, the culture media is acidified by addition of HCl or glacial acetic acid to convert dissolved acrylate to acrylate. Acrylate is then extracted into an equal volume of methylene chloride and detected by analysis on a GC/MS (Hewlett Packard 6890 GC/5972 MSD). One microliter of organic phase is injected onto an HP Agilent J&W DB-FFAP column (30 m length×0.25 mm i.d.×0.25 µm film, oven program 90° C. 5 min, 10° C. min-1 to 140° C., 25° C. min-1 to 240° C., 240° C. 6 min). Peak integration is compared to a reference using purified acrylate standards for quantification. The parent *C. tropicalis* is used as a negative control to assess increased acrylate production by the recombinant cells.

EXAMPLE 6

Production of 3-HP from Alkanes in *Rhodococcus* spp

To create a bacterial strain suitable for production of acrylate or acrylate intermediates from odd-numbered alkanes, the alkane-assimilating microorganism *Rhodococcus opacus* is engineered to reduce its ability to assimilate propionyl-CoA (note that a wide range of *Rhodococcus* species and derivatives are available which would be amenable to this approach). The genetic loci containing accA (ROP_16130) and pccB (ROP_35640, ROP_63560) are deleted in order to inactivate acyl-coA carboxylase and propionyl-CoA carboxylase, respectively. Methods for constructing genetic deletions in *R. opacus* through homologous recombination are well-known in the art, for example Alvarez et al. Microbiology (2008) p. 2327-2335.

To verify the capability of the cells to perform biotransformation of alkanes, individual colonies of *R. opacus* (accA− pccB−) are first streaked onto Luria-Bertani (LB) agar plates (Teknova), and incubated overnight at 30° C. The colonies are then cultured aerobically at 30° C. in liquid media in the presence of 1% (v/v) pentane. Propionate (and 3-HP) accumulation in the culture media is assessed using a GC/MS method. Specifically, the culture media is acidified by addition of HCl or glacial acetic acid to convert dissolved propionate to propionic acid. Propionic acid is then extracted into an equal volume of methylene chloride and detected by analysis on a GC/MS (Hewlett Packard 6890 GC/5972 MSD). One microliter of organic phase is injected onto an HP Agilent J&W DB-FFAP column (30 m length× 0.25 mm i.d.×0.25 µm film, oven program 90° C. 5 min, 10° C. min-1 to 140° C., 25° C. min-1 to 240° C., 240° C. 6 min). Peak integration is compared to a reference using purified propionic acid standards for quantification. The parent *R. opacus* (accA+ pccB+) is used as a negative control to assess increased propionate production by the double knockout mutant.

As *R. opacus* contains a native acyl-CoA oxidase, enoyl-CoA hydratase, and hydrolase, 3-HP production will occur without further engineering. However, a synthetic pathway is engineered into the strain to improve production efficiency. In one instance, an engineered pathway simultaneously expresses a ω-cytochrome P450 and a hydrolase. In this case, intracellular propionyl-CoA is first converted into 3-hydroxypropionyl-CoA (3-HP-CoA). The subsequent CoA cleavage by the hydrolase enzyme yields 3-HP. In order to obtain a highly functional pathway, pathway variants comprising genes from various origins using a combinatorial approach is constructed. For example, a two-enzyme pathway whereby five gene sequences are used for each gene yields a total of 25 pathway variants. The expression of each enzyme in a single cassette is modulated independently using standard bacterial promoters, including the tac promoter or other sigma-70 dependent promoters. In all cases, cassettes are synthesized de novo (DNA2.0) prior to cloning into a plasmid such as pSKsym or pBBR1 (see Plaggenborg et al. Appl. Gen. Mol. Biotech. (2006) p. 745-755. Plasmids containing the combinatorial-enzyme cassettes are then transformed into *R. opacus* (accA− pccB−). Positive transformants are then selected on LB media plus tetracycline (Teknova). Individual colonies are cultured aerobically at 30° C. in liquid media in the presence of alkanes, for example, 1% (v/v) pentane. 3-HP production by the engineered strains are quantified by analyzing the culture media using a GC/MS method. Specifically, the culture media (where one would expect the 3-HP) is acidified by addition of HCl or glacial acetic acid. 3-HP is then extracted into an equal volume methylene chloride. Extracted 3-HP is detected by analysis on a GC/MS (Hewlett Packard 6890 GC/5972 MSD). One microliter of organic phase is injected onto HP Agilent J&W DB-FFAP column (30 m length×0.25 mm i.d.×0.25 µm film, oven program 90° C. 5 min, 10° C. min-1 to 140° C., 25° C. min-1 to 240° C., 240° C. 6 min). Peak integration is compared to the reference using authentic compound for quantification.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

What is claimed is:

1. A genetically engineered alkane-metabolizing bacteria or yeast, comprising:
   (a) a polynucleotide encoding an enzyme that can hydroxylate an omega carbon of an alkane or a β-oxidation product thereof; and
   (b) a genetic alteration to a polynucleotide encoding a propionyl-CoA carboxylase, to a polynucleotide encoding a 2-methylcitrate synthase, or to both, wherein the genetic alteration inactivates the encoded propionyl-CoA carboxylase, 2-methylcitrate synthase, or both,
   wherein the genetically engineered alkane-metabolizing bacteria or yeast accumulate an increased level of propionyl-CoA when cultured in the presence of the alkane under conditions and for a time sufficient to produce propionyl-CoA as compared to a parent bacteria or yeast, respectively, cultured under the same conditions.

2. The genetically engineered alkane-metabolizing bacteria or yeast of claim 1, wherein the alkane is pentane and the enzyme that can hydroxylate the omega carbon of the alkane or β-oxidation product thereof is selected from:
   (a) an enzyme capable of converting pentane to 5-hydroxypentane;
   (b) an enzyme capable of converting pentanoic acid to 5-hydroxypentanoic acid;
   (c) an enzyme capable of converting pentanyl-CoA into 5-hydroxypentanyl CoA; or
   (d) an enzyme capable of converting propionyl-CoA to 3-hydroxypropionyl CoA.

3. The genetically engineered alkane-metabolizing bacteria or yeast of claim 1, wherein the enzyme that can hydroxylate the omega carbon of the alkane or β-oxidation product thereof has an amino acid sequence that is at least 80% identical to the amino acid sequence of a cytochrome P450 enzyme selected from Table 1, or is an alkane oxidase enzyme.

4. The genetically engineered alkane-metabolizing bacteria or yeast of claim 1, wherein the enzyme that can hydroxylate an omega carbon of an alkane or a β-oxidation product thereof is native to the bacteria or yeast.

5. The genetically engineered alkane-metabolizing bacteria or yeast of claim 1, wherein the enzyme that can hydroxylate the omega carbon of an alkane or a β-oxidation product thereof is non-native to the bacteria or yeast.

6. The genetically engineered alkane-metabolizing bacteria or yeast of claim 1, further comprising a 3-hydroxyisobutyryl-CoA hydrolase capable of converting 3-hydroxypropionyl CoA to 3-hydroxypropionate.

7. The genetically engineered alkane-metabolizing bacteria or yeast of claim 1, further comprising a propionyl-CoA dehydrogenase capable of converting propionyl-CoA to acrylyl-CoA.

8. The genetically engineered alkane-metabolizing bacteria or yeast of claim 7, further comprising a 3-hydroxypropionyl-CoA dehydratase capable of converting the acrylyl-CoA to 3-hydroxypropionyl-CoA.

9. The genetically engineered alkane-metabolizing bacteria or yeast of claim 7, further comprising an acyl-CoA hydrolase capable of converting acrylyl-CoA to acrylate.

10. The genetically engineered alkane-metabolizing bacteria or yeast of claim 9, further comprising a genetic alteration to a polynucleotide encoding a 3-hydroxypropionyl-CoA dehydratase, to a polynucleotide encoding a lactyl-CoA dehydratase, or to both, wherein the genetic alteration inactivates, respectively, the 3-hydroxypropionyl-CoA dehydratase, the lactyl-CoA dehydratase, or both.

11. The genetically engineered alkane-metabolizing bacteria or yeast of claim 7, further comprising a 3-hydroxyisobutyryl-CoA hydrolase capable of converting 3-hydroxypropionyl-CoA to 3-hydroxypropionate.

12. The genetically engineered alkane-metabolizing bacteria or yeast of claim 11, further comprising a genetic alteration that to a polynucleotide encoding: (a) a 3-hydroxyisobutyrate dehydrogenase; (b) an aldehyde dehydrogenase; (c) an acetyl-CoA carboxylase; (d) a malonyl-CoA reductase; or (e) any combination thereof, wherein the genetic alteration inactivates the encoded enzyme(s) of (a) to (e).

13. The genetically engineered alkane-metabolizing bacteria or yeast of claim 1, further comprising genetic alteration to a polynucleotide encoding: (a) a 3-hydroxyisobutyrate dehydrogenase; (b) an aldehyde dehydrogenase; (c) an acetyl-CoA carboxylase; (d) a malonyl-CoA reductase; (e) a 3-hydroxypropionyl-CoA dehydratase; (f) a lactyl-CoA dehydratase, or (g) any combination thereof, wherein the genetic alteration inactivates the encoded enzyme(s) of (a) to (g).

14. The genetically engineered alkane-metabolizing bacteria or yeast of claim 13, wherein the genetically engineered alkane-metabolizing bacteria or yeast accumulates an increased level of propionyl-CoA when the genetically engineered alkane metabolizing bacteria or yeast is cultured in the presence of the alkane under conditions and for a time sufficient to produce propionyl-CoA as compared to the genetically engineered alkane-metabolizing bacteria or yeast of claim 1, respectively, cultured under the same conditions.

15. The genetically engineered alkane-metabolizing bacteria or yeast of claim 1, wherein the genetic alteration results in an inactivated propionyl-CoA carboxylase gene, an inactivated 2-methylcitrate synthase gene, or both.

16. The genetically engineered alkane-metabolizing bacteria or yeast of claim 1, wherein the genetically engineered alkane-metabolizing bacteria or yeast is a genetically engineered alkane-metabolizing bacteria.

17. The genetically engineered alkane-metabolizing bacteria or yeast of claim 16, wherein the genetically engineered alkane-metabolizing bacteria is from a genus of *Pseudomonas, Corynebacterium*, or *Rhodococcus*.

18. The genetically engineered alkane-metabolizing bacteria or yeast of claim 1, wherein the genetically engineered alkane-metabolizing bacteria or yeast is a genetically engineered alkane-metabolizing yeast.

19. The genetically engineered alkane-metabolizing bacteria or yeast of claim 18, wherein the genetically engineered alkane-metabolizing yeast is from a genus of *Candida, Yarrowia*, or *Saccharomyces*.

20. A method for making 3-hydroxypropionate or acrylate, comprising culturing the genetically engineered alkane-metabolizing bacteria or yeast of claim 1 in a culture medium comprising an odd numbered chain alkane for a time sufficient to allow the genetically engineered alkane-metabolizing bacteria or yeast to produce 3-hydroxypropionyl CoA or acrylyl-CoA.

21. The method of claim 20, wherein the odd-numbered chain alkane is a heptane, a pentane or a propane.

22. The method of claim 20, further comprising harvesting the genetically engineered alkane-metabolizing bacteria or yeast and generating a lysate of the harvested genetically engineered alkane-metabolizing bacteria or yeast.

23. The method of claim 22, further comprising isolating 3-hydroxypropionyl-CoA or acrylyl-CoA from the lysate.

24. The method of claim 22, further comprising treating the lysate with an acid or base, thereby hydrolyzing the 3-hydroxypropionyl-CoA to produce the 3-hydroxypropionate or thereby hydrolyzing the acrylyl-CoA to produce acrylate.

25. The method of claim 24, further comprising converting the 3-hydroxypropionate to acrylate.

26. The method of claim 20, further comprising treating the culture medium with an acid or base, thereby hydrolyzing the 3-hydroxypropionyl-CoA to produce 3-hydroxypropionate or thereby hydrolyzing the acrylyl-CoA to produce acrylate.

27. The method of claim 26, further comprising converting the 3-hydroxypropionate to acrylate.

28. The method of claim 20, wherein the enzyme that can hydroxylate the omega carbon of the alkane or β-oxidation product thereof has an amino acid sequence that is at least 80% identical to the amino acid sequence of a cytochrome P450 enzyme selected from Table 1, or is an alkane oxidase enzyme.

* * * * *

UNITED STATES PATENT AND TRADEMARK OFFICE
CERTIFICATE OF CORRECTION

PATENT NO. : 9,657,317 B2  
APPLICATION NO. : 14/344899  
DATED : May 23, 2017  
INVENTOR(S) : Joshua A. Silverman et al.

Page 1 of 1

It is certified that error appears in the above-identified patent and that said Letters Patent is hereby corrected as shown below:

In the Claims

<u>Column 27, Line 5:</u>
"alteration that to a polynucleotide encoding: (a) a 3-hydroxyisobutyrate" should read, --alteration to a polynucleotide encoding: (a) a 3-hydroxyisobutyrate--.

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 3

<210> SEQ ID NO 1
<211> LENGTH: 2932
<212> TYPE: DNA
<213> ORGANISM: Artificial sequence
<220> FEATURE:
<223> OTHER INFORMATION: Synthetic construct

<400> SEQUENCE: 1
cgcggaggac ccagtgtaac acctcacgac tcttctgaac ttcacctctt cccacacaac      60
agtcgacacc atatcatata aaactaacaa tgcattgctt attacgaaga ctaccgttg     120 ctatctccac accgttatct ccacggtcca aaggctgctc aatgtgctgc atacgtaacg    180
tggggtgcaa ccttgagcac atagtacttt tccgaaaacc ggcgataatt aagtgtgcac    240
tccaactttt cacactgagc gtaaaatgtg gagaagaaat cggcactaaa aagtcaggta    300
gactggaaaa tgcgccatga aatgaatatc tcttgctaca gtaatgccca gcatcgaggg    360
gtattgtgtc accaacacta tagtggcagc tgaagcgctc gtgattgtag tatgagtctt    420
tattggtgat gggaagagtt cactcaatat tctcgttact gccaaaacac cacggtaatc    480
ggccagacac catggatgta gatcaccaag cctgtgaatg ttattcgagc taaaatgcac    540
atggttggtg aaaggagtag ttgctgtcga attccgtcgt cgcctgagtc atcatttatt    600
taccagttgg ccacaaaccc ttgacgatct cgtatgtccc ctccgacata ctcccggccg    660 gctgggtac gttcgatagc gctatcggca tcgacaaggt ttgggtccct agccgatacc    720
gcactacctg agtcacaatc ttcggaggtt tagtcttcca catagcacgg gcaaaagtgc    780
gtatatatac aagagcgttt gccagccaca gattttcact ccacacacca catcacacat    840
acaaccacac acatccacaa tggaacccga aactaagaag accaagactg actccaagaa    900
gattgttctt ctcggcggcg acttctgtgg ccccgaggtg attgccgagg ccgtcaaggt    960
gctcaagtct gttgctgagg cctccggcac cgagtttgtg tttgaggacc gactcattgg   1020
aggagctgcc attgagaagg agggcgagcc catcaccgac gctactctcg acatctgccg   1080
aaaggctgac tctattatgc tcggtgctgt cggaggcgct gccaacaccg tatggaccac   1140
tcccgacgga cgaaccgacg tgcgacccga gcagggtctc ctcaagctgc gaaaggacct   1200
gaacctgtac gccaacctgc gaccctgcca gctgctgtcg cccaagctcg ccgatctctc   1260
ccccatccga aacgttgagg gcaccgactt catcattgtc cgagagctcg tcggaggtat   1320
ctactttgga gagcgaaagg aggatgacgg atctggcgtc gcttccgaca ccgagaccta   1380
ctccgttcct gaggttgagc gaattgcccg aatgccgcc ttcctggccc ttcagcacaa    1440 ccccctctt cccgtgtggt ctcttgacaa ggccaacgtg ctggcctcct ctcgactttg    1500
```

```
gcgaaagact gtcactcgag tcctcaagga cgaattcccc cagctcgagc tcaaccacca    1560
gctgatcgac tcggccgcca tgatcctcat caagcagccc tccaagatga atggtatcat    1620
catcaccacc aacatgtttg gcgatatcat ctccgacgag gcctccgtca tccccggttc    1680
tctgggtctg ctgccctccg cctctctggc ttctctgccc gacaccaacg aggcgttcgg    1740
tctgtacgag ccctgtcacg gatctgcccc cgatctcggc aagcagaagg tcaaccccat    1800
tgccaccatt ctgtctgccg ccatgatgct caagttctct cttaacatga gcccgccgg    1860 tgacgctgtt gaggctgccg tcaaggagtc cgtcgaggct ggtatcacta ccgccgatat    1920
cggaggctct tcctccacct ccgaggtcgg agacttgttg ccaacaaggt caaggagctg    1980
ctcaagaagg agtaagtcgt ttctacgacg cattgatgga aggagcaaac tgacgcgcct    2040
gcgggttggc ctaccggcag gtccgctag tgtataagac tctataaaaa gggccctgcc    2100
ctgctaatga aatgatgatt tataatttac cggtgtagca accttgacta gaagaagcag    2160
attgggtgtg tttgtagtgg aggacagtgg tacgttttgg aaacagtctt cttgaaagtg    2220
tcttgtctac agtatattca ctcataacct caatagccaa gggtgtagtc ggtttattaa    2280
aggaagggag ttgtggctga tgtggataga tatctttaag ctggcgactg cacccaacga    2340
gtgtggtggt agcttgttac tgtatattcg gtaagatata ttttgtgggg ttttagtggt    2400
gtttggtagg ttagtgcttg gtatatgagt tgtaggcatg acaatttgga aaggggtgga    2460
ctttgggaat attgtgggat ttcaatacct tagtttgtac agggtaattg ttacaaatga    2520
tacaaagaac tgtatttctt ttcatttgtt ttaattggtt gtatatcaag tccgttagac    2580
gagctcagtg ccatggcttt tggcactgta tttcattttt agaggtacac tacattcagt    2640
gaggtatggt aaggttgagg gcataatgaa ggcaccttgt actgacagtc acagacctct    2700
caccgagaat tttatgagat atactcgggt tcattttagg ctccgattcg attcaaatta    2760
ttactgtcga aatcggttga gcatccgttg atttccgaac agatctcggc agtctctcgg    2820
atgtagaatt aggtttcctt gaggcgaaga tcggtttgtg tgacatgaat tggggatttg    2880
ggcgcaggca tgtatttagg actagaataa aatgattata aggaacgaac cg            2932
```

<210> SEQ ID NO 2
<211> LENGTH: 2941
<212> TYPE: DNA
<213> ORGANISM: Artificial sequence
<220> FEATURE:
<223> OTHER INFORMATION: Synthetic sequence

<400> SEQUENCE: 2

```
ggaagtgagc ctgcccgctc tgaacaaggt ctagagtctt cgtaactaac cccacacaca      60
tcaacacagt cgacaccata tcatataaaa ctaacaatgc attgcttatt acgaagacta     120
cccgttgcta tctccacacc gttatctcca cggtccaaag gctgctcaat gtgctgcata     180
cgtaacgtgg ggtgcaacct tgagcacata gtacttttcc gaaaaccggc gataattaag     240
tgtgcactcc aacttttcac actgagcgta aaatgtggag aagaaatcgg cactaaaaag     300
tcaggtagac tggaaaatgc gccatgaaat gaatatctct tgctacagta atgcccagca     360
tcgaggggta ttgtgtcacc aacactatag tggcagctga agcgctcgtg attgtagtat     420
gagtctttat tggtgatggg aagagttcac tcaatattct cgttactgcc aaaacaccac     480
ggtaatcggc cagacaccat ggatgtgat caccaagcct gtgaatgtta ttcgagctaa      540
aatgcacatg gttggtgaaa ggagtagttg ctgtcgaatt ccgtcgtcgc ctgagtcatc     600
```

```
atttatttac cagttggcca caaacccttg acgatctcgt atgtcccctc cgacatactc    660
ccggccggct ggggtacgtt cgatagcgct atcggcatcg acaaggtttg ggtccctagc    720
cgataccgca ctacctgagt cacaatcttc ggaggtttag tcttccacat agcacgggca    780
aaagtgcgta tatatacaag agcgtttgcc agccacagat tttcactcca cacaccacat    840
cacacataca accacacaca tccacaatgg aacccgaaac taagaagacc aagactgact    900
ccaagaagat tgttcttctc ggcggcgact tctgtggccc cgaggtgatt gccgaggccg    960
tcaaggtgct caagtctgtt gctgaggcct ccggcaccga gtttgtgttt gaggaccgac   1020
tcattggagg agctgccatt gagaaggagg gcgagcccat caccgacgct actctcgaca   1080
tctgccgaaa ggctgactct attatgctcg gtgctgtcgg aggcgctgcc aacaccgtat   1140
ggaccactcc cgacggacga accgacgtgc gacccgagca gggtctcctc aagctgcgaa   1200
aggacctgaa cctgtacgcc aacctgcgac cctgccagct gctgtcgccc aagctcgccg   1260
atctctcccc catccgaaac gttgagggca ccgacttcat cattgtccga gagctcgtcg   1320
gaggtatcta ctttggagag cgaaaggagg atgacggatc tggcgtcgct tccgacaccg   1380
agacctactc cgttcctgag gttgagcgaa ttgcccgaat ggccgccttc ctggcccttc   1440
agcacaaccc ccctcttccc gtgtggtctc ttgacaaggc caacgtgctg gcctcctctc   1500
gactttggcg aaagactgtc actcgagtcc tcaaggacga attcccccag ctcgagctca   1560
accaccagct gatcgactcg gccgccatga tcctcatcaa gcagccctcc aagatgaatg   1620
gtatcatcat caccaccaac atgtttggcg atatcatctc cgacgaggcc tccgtcatcc   1680
ccggttctct gggtctgctg ccctccgcct ctctggcttc tctgcccgac accaacgagg   1740
cgttcggtct gtacgagccc tgtcacggat ctgccccccga tctcggcaag cagaaggtca   1800
accccattgc caccattctg tctgccgcca tgatgctcaa gttctctctt aacatgaagc   1860
ccgccggtga cgctgttgag gctgccgtca aggagtccgt cgaggctggt atcactaccg   1920
ccgatatcgc aggctcttcc tccacctccg aggtcggaga cttgttgcca acaaggtcaa   1980
ggagctgctc aagaaggagt aagtcgtttc tacgacgcat tgatggaagg agcaaactga   2040
cgcgcctgcg ggttggtcta ccggcagggt ccgctagtgt ataagactct ataaaaaggg   2100
ccctgccctg ctaatgaaat gatgatttat aatttaccgg tgtagcaacc ttgactagaa   2160
gaagcagatt gggtgtgttt gtagtggagg acagtggtac gttttggaaa cagtcttctt   2220
gaaagtgtct tgtctacagt atattcactc ataacctcaa tagccaaggg tgtagtcggt   2280
ttattaaagg aagggagttg tggctgatgt ggatagatat ctttaagctg gcgactgcac   2340
ccaacgagtg tggtggtagc ttgttactgt atattcggta agatatattt tgtggggttt   2400
tagtggtgtt tggtaggtta gtgcttggta tatgagttgt aggcatgaca atttggaaag   2460
gggtggactt tgggaatatt tgggatttc aatacccttag tttgtacagg gtaattgtta   2520
caaatgatac aaagaactgt atttcttttc atttgtttta attggttgta tatcaagtcc   2580
gttagacgag ctcagtgcca tggcttttgg cactgtattt catttttaga ggtacactac   2640
attcagtgag gtatggtaag gttgagggca taatgaaggc accttgtact gacagtcaca   2700
gacctctcac cgagaatttt atgagatata ctcgggttca ttttaggctc cgattcgatt   2760
caaattatta ctgtcgaaat cggttgagca tccgttgatt tccgaacaga tctcggcagt   2820
ctctcggatg tagaattagg tttccttgag gcgaagatcg gtttgtgtga catgaattgc   2880
gaagtatagt tgatatgatt tacgatgttt tgagcaagca caagcacgag atgcttgtaa   2940
g                                                                  2941
```

```
<210> SEQ ID NO 3
<211> LENGTH: 714
<212> TYPE: DNA
<213> ORGANISM: artificial sequence
<220> FEATURE:
<223> OTHER INFORMATION: synthetic gene

<400> SEQUENCE: 3
atggttaccg ccctgacgga aggtgctaag ctctttgaga aggaaatccc ctacattact      60
gagcttgaag gcgacgtgga gggaatgaag ttcatcatta agggtgaggg tacaggtgac     120
gccaccaccg gcacgattaa ggccaagtac atctgtacta cggggggattt gcctgtgccg    180 tgggctactc tcgtcagtac cctgtcatat ggtgtccagt gcttcgctaa gtaccctct     240 catatcaagg acttttcaa atccgcaatg cccgagggct acactcagga gcgaacaatt    300
tcgtttgagg gcgatggagt ctacaagacc cgagctatgg tgacctacga gcgaggaagc    360
atctacaaca gagttactct gaccggcgag aacttcaaaa aggatggaca cattctgagg    420
aaaaacgtgg ccttccagtg ccctccctct attctgtaca ttctacccga caccgtcaac    480
aatggaatcc gggtcgagtt taaccaagcc tacgacatcg agggcgttac ggaaaagctc    540
gtaaccaaat gttctcagat gaatagacct ctcgctggat cggcagccgt ccatatccca    600
cggtatcacc acattactta ccatacaaag ttgtccaagg accgtgatga gcgacgcgac    660
cacatgtgcc tggtggaagt ggttaaggcg gtggatcttg acacatatca gtaa           714
```